US012806271B2

(12) United States Patent
Shiku et al.

(10) Patent No.: US 12,806,271 B2
(45) Date of Patent: Nov. 24, 2026

(54) PRAME BINDING MOLECULE

(71) Applicant: MIE UNIVERSITY, Tsu (JP)

(72) Inventors: Hiroshi Shiku, Tsu (JP); Yasushi Akahori, Tsu (JP); Hiroyuki Hiratsuka, Tsu (JP)

(73) Assignee: MIE UNIVERSITY, Tsu (JP)

( * ) Notice: Subject to any disclaimer, the term of this patent is extended or adjusted under 35 U.S.C. 154(b) by 710 days.

(21) Appl. No.: 18/266,340

(22) PCT Filed: Dec. 7, 2021

(86) PCT No.: PCT/JP2021/044807
§ 371 (c)(1),
(2) Date: Jun. 9, 2023

(87) PCT Pub. No.: WO2022/124282
PCT Pub. Date: Jun. 16, 2022

(65) Prior Publication Data

US 2024/0024480 A1 Jan. 25, 2024

(30) Foreign Application Priority Data

Dec. 10, 2020 (JP) ................................ 2020-205384

(51) Int. Cl.

| | |
|---|---|
| ***A61K 40/42*** | (2025.01) |
| ***A61K 40/11*** | (2025.01) |
| ***A61K 40/31*** | (2025.01) |
| ***A61K 40/32*** | (2025.01) |
| ***A61P 35/00*** | (2006.01) |
| ***C07K 14/705*** | (2006.01) |
| ***C07K 16/32*** | (2006.01) |
| ***C12N 5/0783*** | (2010.01) |
| ***C12N 15/86*** | (2006.01) |

(52) U.S. Cl.
CPC .......... *A61K 40/4271* (2025.01); *A61K 40/11* (2025.01); *A61K 40/31* (2025.01); *A61K 40/32* (2025.01); *A61K 40/427* (2025.01); *A61P 35/00* (2018.01); *C07K 14/7051* (2013.01); *C07K 16/32* (2013.01); *C12N 5/0636* (2013.01); *C12N 15/86* (2013.01); *A61K 2239/31* (2023.05); *A61K 2239/38* (2023.05); *A61K 2239/57* (2023.05); *C07K 2317/622* (2013.01); *C07K 2319/03* (2013.01); *C12N 2740/10043* (2013.01)

(58) Field of Classification Search
CPC .... A61K 40/4271; A61K 40/11; A61K 40/31; A61K 40/32; A61K 40/427; A61K 2239/31; A61K 2239/38; A61K 2239/57; A61K 40/4211; A61K 2239/46; A61K 2039/505; A61P 35/00; C07K 14/7051; C07K 16/32; C07K 2317/622; C07K 2319/03; C07K 2317/34; C07K 2317/56; C07K 2317/565; C07K 2317/92; C07K 16/3053; C07K 16/30; C12N 5/0636; C12N 15/86; C12N 2740/10043; C12N 2510/00; C12N 2740/13043; C40B 40/10
See application file for complete search history.

(56) References Cited

U.S. PATENT DOCUMENTS

2020/0276237 A1 9/2020 Shiku et al.

FOREIGN PATENT DOCUMENTS

| | | | |
|---|---|---|---|
| CN | 106478809 | A | 3/2017 |
| CN | 110709516 | A | 1/2020 |
| CN | 111690050 | A | 9/2020 |
| WO | 2016191246 | A2 | 12/2016 |

OTHER PUBLICATIONS

Orlando et al. Adoptive Immunotherapy Using PRAME-Specific T Cells in Medulloblastoma. Cancer Res. Jun. 15, 2018;78(12):3337-3349. (Year: 2018).*
Pankov et al. In vivo immuno-targeting of an extracellular epitope of membrane bound preferentially expressed antigen in melanoma (PRAME). Oncotarget. Jul. 26, 2017;8(39):65917-65931. (Year: 2017).*
Akahori et al., "Isolation of antigen/antibody complexes through organic solvent (ICOS) method", Biochemical and Biophysical Research Communications, (2009), vol. 378, pp. 832-835.
International Search Report dated Jan. 11, 2022 for corresponding International Application No. PCT/JP2021/044807, 7 pages (with English translation).

(Continued)

*Primary Examiner* — Gary B Nickol
*Assistant Examiner* — Amber K Faust
(74) *Attorney, Agent, or Firm* — MH2 Technology Law Group, LLP

(57) ABSTRACT

An object is to provide a PRAME-binding molecule. This object is achieved by a PRAME-binding molecule comprising a heavy-chain variable region containing a heavy-chain CDR1 comprising the amino acid sequence represented by SEQ ID NO: 1, a heavy-chain CDR2 comprising the amino acid sequence represented by SEQ ID NO: 2, and a heavy-chain CDR3 comprising the amino acid sequence represented by SEQ ID NO: 3, and/or a light-chain variable region containing a light-chain CDR1 comprising the amino acid sequence represented by SEQ ID NO: 9, a light-chain CDR2 comprising the amino acid sequence represented by SEQ ID NO: 10, and a light-chain CDR3 comprising the amino acid sequence represented by SEQ ID NO: 11.

12 Claims, 22 Drawing Sheets

Specification includes a Sequence Listing.

(56) References Cited

OTHER PUBLICATIONS

Van Baren, et al., "PRAME, a gene encoding an antigen recognized on a human melanoma by cytolytic T cells, is expressed in acute leukaemia cells", British Journal Haematology, (1998), vol. 102, pp. 1376-1379.
Neumann et al., "Heterogeneous expression of the tumor-associated antigens RAGE-1, PRAME, and glycoprotein 75 In human renal cell carcinoma candidates for T-cell-based immunotherapies?" Cancer Research, (1998), vol. 58, pp. 4090-4095.
Pellat-Deceunynck et al., "The cancer germ-line genes MAGE-1, MAGE-3 and PRAME are commonly expressed by human myeloma cells", Eur. Journal Immunol., (2000), vol. 30, pp. 803-809.
Kessler et al., "Efficient Identification of Novel Hla-A*0201-Presented Cytotoxic T Lymphocyte Epitopes in the Widely Expressed Tumor Antigen Prame by Proteasome-Mediated Digestion Analysis", J. Exp. Med., (2001),vol. 193(1), pp. 73-88.
Quintarelli et al., "High-avidity cytotoxic T lymphocytes specific for a new PRAME-derived peptide can target leukemic and leukemic precursor cells", Blood, (2011), vol. 117(12), pp. 3353-3362.
Ikeda et al., "Characterization of an Antigen That is Recognized on a Melanoma Showing Partial HLA Loss by CTL Expressing an NK Inhibitory Receptor", Immunity, (1997), vol. 6, pp. 199-208.
Akahori et al., 2018, "Antitumor activity of CAR-T cells targeting the intracellular oncoprotein WT1 can be enhanced by vaccination", Blood, 2018, vol. 132(11), pp. 1134-1145.
Akahori et al., "Isolation of antigen/antibody complexes through organic solvent (ICOS) method", Biochemical and Biophysical Research Communications, (2009), vol. 398, pp. 832-835.
Hiratsuka et al., "Development of TCR-like CAR-T cells targeting the cancer testis antigen PRAME p 301-309/HLA-A*24:02", The 25th Annual Meeting of the Japanese Cancer Immunology Society Program, Jul. 2, 2021, Y3-4 (partial English language translation).
Office Action issued Jul. 2, 2026 in the corresponding Chinese Application No. 202180083394.X, with English translation, (12 pages total).

* cited by examiner

Experiment Name: 181219peptide pulse cp3formA24
Tube Name: #98 new Ab non pulse
Record Date: Dec 19, 2018 2:51:34 PM

| Population | #Events | %Parent | FITC-A Mean |
|---|---|---|---|
| All Events | 30,000 | #### | 412 |
| MiyaharaLCL | 18,598 | 62.0 | 368 |

Experiment Name: 181219peptide pulse cp3formA24
Tube Name: #98 new Ab PRAME
Record Date: Dec 19, 2018 2:53:42 PM

| Population | #Events | %Parent | FITC-A Mean |
|---|---|---|---|
| All Events | 30,000 | #### | 4,709 |
| MiyaharaLCL | 18,633 | 62.1 | 4,367 |

#98 zG CAR

Color intensity

| | | |
|---|---|---|
| White | NW-MEL-38-A24 (PRAME+ HLA-A24+) |
| Light gray | NGM |
| Gray | CD19CAR-T |
| Black | #98zG |

SEQUENCE LISTING

```
<160> NUMBER OF SEQ ID NOS: 40

<210> SEQ ID NO 1
<211> LENGTH: 8
<212> TYPE: PRT
<213> ORGANISM: Artificial Sequence
<220> FEATURE:
<223> OTHER INFORMATION: H CDR1

<400> SEQUENCE: 1

Gly Gly Thr Phe Ser Ser Tyr Ala
1               5


<210> SEQ ID NO 2
<211> LENGTH: 8
<212> TYPE: PRT
<213> ORGANISM: Artificial Sequence
<220> FEATURE:
<223> OTHER INFORMATION: H CDR2

<400> SEQUENCE: 2

Ile Ile Pro Ile Phe Gly Thr Ala
1               5


<210> SEQ ID NO 3
<211> LENGTH: 14
<212> TYPE: PRT
<213> ORGANISM: Artificial Sequence
<220> FEATURE:
<223> OTHER INFORMATION: H CDR3

<400> SEQUENCE: 3

Ala Arg His His Ser Asn Tyr Tyr Tyr Tyr Gly Met Asp Val
1               5                   10


<210> SEQ ID NO 4
<211> LENGTH: 121
<212> TYPE: PRT
<213> ORGANISM: Artificial Sequence
<220> FEATURE:
<223> OTHER INFORMATION: H variable region

<400> SEQUENCE: 4
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Gly Thr Ala Tyr
65                  70                  75                  80

Met Glu Leu Ser Ser Leu Arg Ser Glu Asp Thr Ala Val Tyr Tyr Cys
                85                  90                  95

Ala Arg His His Ser Asn Tyr Tyr Tyr Tyr Gly Met Asp Val Trp Gly
            100                 105                 110

Gln Gly Thr Thr Val Thr Val Ser Arg
        115                 120
```

<210> SEQ ID NO 5
<211> LENGTH: 24
<212> TYPE: DNA
<213> ORGANISM: Artificial Sequence
<220> FEATURE:
<223> OTHER INFORMATION: H CDR1

<400> SEQUENCE: 5

```
ggaggcacct tcagcagcta tgct                                            24
```

<210> SEQ ID NO 6
<211> LENGTH: 24
<212> TYPE: DNA
<213> ORGANISM: Artificial Sequence
<220> FEATURE:
<223> OTHER INFORMATION: H CDR2

<400> SEQUENCE: 6

```
atcatcccta tctttggtac agca                                            24
```

<210> SEQ ID NO 7
<211> LENGTH: 42
<212> TYPE: DNA
<213> ORGANISM: Artificial Sequence
<220> FEATURE:
<223> OTHER INFORMATION: H CDR3

<400> SEQUENCE: 7

```
gcgagacacc acagtaacta ctactactac ggtatggacg tc                        42
```

<210> SEQ ID NO 8
<211> LENGTH: 363
<212> TYPE: DNA
<213> ORGANISM: Artificial Sequence
<220> FEATURE:
<223> OTHER INFORMATION: H variable region

<400> SEQUENCE: 8

```
caggtgcagc tggtgcagtc tggggctgag gtgaagaagc ctgggtcctc ggtgaaggtc     60

tcctgcaagg cttctggagg caccttcagc agctatgcta tcagctgggt gcgacaggcc    120

cctggacaag ggcttgagtg gatgggaggg atcatcccta tctttggtac agcaaactac    180

gcacagaagt tccagggcag agtcacgatt accgcggacg aatccacggg cacagcctac    240

atggagctga gcagcctgag atctgaggac acggccgtgt attactgtgc gagacaccac    300
```

```
agtaactact actactacgg tatggacgtc tggggccaag ggaccacggt caccgtctcg    360

aga                                                                  363


<210> SEQ ID NO 9
<211> LENGTH: 6
<212> TYPE: PRT
<213> ORGANISM: Artificial Sequence
<220> FEATURE:
<223> OTHER INFORMATION: L CDR1

<400> SEQUENCE: 9

Asn Ile Gly Ser Lys Asn
1               5


<210> SEQ ID NO 10
<211> LENGTH: 3
<212> TYPE: PRT
<213> ORGANISM: Artificial Sequence
<220> FEATURE:
<223> OTHER INFORMATION: L CDR2

<400> SEQUENCE: 10

Arg Asp Ser
1


<210> SEQ ID NO 11
<211> LENGTH: 8
<212> TYPE: PRT
<213> ORGANISM: Artificial Sequence
<220> FEATURE:
<223> OTHER INFORMATION: L CDR3

<400> SEQUENCE: 11

Gln Val Trp Asp Ser Ser His Val
1               5


<210> SEQ ID NO 12
<211> LENGTH: 105
<212> TYPE: PRT
<213> ORGANISM: Artificial Sequence
<220> FEATURE:
<223> OTHER INFORMATION: L variable region

<400> SEQUENCE: 12

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser His Val Phe
                85                  90                  95

Gly Thr Gly Thr Lys Val Thr Val Leu
            100                 105


<210> SEQ ID NO 13
<211> LENGTH: 18
<212> TYPE: DNA
```

<213> ORGANISM: Artificial Sequence
<220> FEATURE:
<223> OTHER INFORMATION: L CDR1

<400> SEQUENCE: 13
aacattggaa gtaaaaat 18

<210> SEQ ID NO 14
<211> LENGTH: 9
<212> TYPE: DNA
<213> ORGANISM: Artificial Sequence
<220> FEATURE:
<223> OTHER INFORMATION: L CDR2

<400> SEQUENCE: 14 agggatagc 9

<210> SEQ ID NO 15
<211> LENGTH: 24
<212> TYPE: DNA
<213> ORGANISM: Artificial Sequence
<220> FEATURE:
<223> OTHER INFORMATION: L CDR3

<400> SEQUENCE: 15
caggtgtggg acagcagcca tgtc 24

<210> SEQ ID NO 16
<211> LENGTH: 315
<212> TYPE: DNA
<213> ORGANISM: Artificial Sequence
<220> FEATURE:
<223> OTHER INFORMATION: L variable region

<400> SEQUENCE: 16
tcctatgagc tgactcagcc actctcagtg tcagtggccc tgggacagac ggccaggatt 60
acctgtggcg gaaacaacat tggaagtaaa aatgtgcact ggtaccagca gaagccaggc 120
caggcccctg tgctggtcat ctatagggat agcaaccggc cctctgggat ccctgagcga 180
ttctctggct ccaactcggg gaacacggcc accctgacca tcagcagagc ccaagccggg 240
gatgaggctg actattactg tcaggtgtgg gacagcagcc atgtcttcgg aactgggacc 300
aaggtcaccg tccta 315

<210> SEQ ID NO 17
<211> LENGTH: 9
<212> TYPE: PRT
<213> ORGANISM: Artificial Sequence
<220> FEATURE:
<223> OTHER INFORMATION: PRAMEp301-309

<400> SEQUENCE: 17

Leu Tyr Val Asp Ser Leu Phe Phe Leu
1 5

<210> SEQ ID NO 18
<211> LENGTH: 9
<212> TYPE: PRT
<213> ORGANISM: Artificial Sequence
<220> FEATURE:
<223> OTHER INFORMATION: PRAME p301-1A

<400> SEQUENCE: 18

Ala Tyr Val Asp Ser Leu Phe Phe Leu
1 5

<210> SEQ ID NO 19
<211> LENGTH: 9
<212> TYPE: PRT
<213> ORGANISM: Artificial Sequence
<220> FEATURE:
<223> OTHER INFORMATION: PRAME p301-2A

<400> SEQUENCE: 19

Leu Ala Val Asp Ser Leu Phe Phe Leu
1               5

<210> SEQ ID NO 20
<211> LENGTH: 9
<212> TYPE: PRT
<213> ORGANISM: Artificial Sequence
<220> FEATURE:
<223> OTHER INFORMATION: PRAME p301-3A

<400> SEQUENCE: 20

Leu Tyr Ala Asp Ser Leu Phe Phe Leu
1               5

<210> SEQ ID NO 21
<211> LENGTH: 9
<212> TYPE: PRT
<213> ORGANISM: Artificial Sequence
<220> FEATURE:
<223> OTHER INFORMATION: PRAME p301-4A

<400> SEQUENCE: 21

Leu Tyr Val Ala Ser Leu Phe Phe Leu
1               5

<210> SEQ ID NO 22
<211> LENGTH: 9
<212> TYPE: PRT
<213> ORGANISM: Artificial Sequence
<220> FEATURE:
<223> OTHER INFORMATION: PRAME p301-5A

<400> SEQUENCE: 22

Leu Tyr Val Asp Ala Leu Phe Phe Leu
1               5

<210> SEQ ID NO 23
<211> LENGTH: 9
<212> TYPE: PRT
<213> ORGANISM: Artificial Sequence
<220> FEATURE:
<223> OTHER INFORMATION: PRAME p301-6A

<400> SEQUENCE: 23

Leu Tyr Val Asp Ser Ala Phe Phe Leu
1               5

<210> SEQ ID NO 24
<211> LENGTH: 9
<212> TYPE: PRT
<213> ORGANISM: Artificial Sequence
<220> FEATURE:
<223> OTHER INFORMATION: PRAME p301-7A

<400> SEQUENCE: 24

Leu Tyr Val Asp Ser Leu Ala Phe Leu
1               5

<210> SEQ ID NO 25
<211> LENGTH: 9
<212> TYPE: PRT
<213> ORGANISM: Artificial Sequence
<220> FEATURE:
<223> OTHER INFORMATION: PRAME p301-8A

<400> SEQUENCE: 25

Leu Tyr Val Asp Ser Leu Phe Ala Leu
1               5

<210> SEQ ID NO 26
<211> LENGTH: 9
<212> TYPE: PRT
<213> ORGANISM: Artificial Sequence
<220> FEATURE:
<223> OTHER INFORMATION: PRAME p301-9A

<400> SEQUENCE: 26

Leu Tyr Val Asp Ser Leu Phe Phe Ala
1               5

<210> SEQ ID NO 27
<211> LENGTH: 9
<212> TYPE: PRT
<213> ORGANISM: Artificial Sequence
<220> FEATURE:
<223> OTHER INFORMATION: PRAME p301-2W

<400> SEQUENCE: 27

Leu Trp Val Asp Ser Leu Phe Phe Leu
1               5

<210> SEQ ID NO 28
<211> LENGTH: 9
<212> TYPE: PRT
<213> ORGANISM: Artificial Sequence
<220> FEATURE:
<223> OTHER INFORMATION: PRAME p301-2F

<400> SEQUENCE: 28

Leu Phe Val Asp Ser Leu Phe Phe Leu
1               5

<210> SEQ ID NO 29
<211> LENGTH: 9
<212> TYPE: PRT
<213> ORGANISM: Artificial Sequence
<220> FEATURE:
<223> OTHER INFORMATION: PRAME p301-9F

<400> SEQUENCE: 29

Leu Tyr Val Asp Ser Leu Phe Phe Phe
1               5

<210> SEQ ID NO 30
<211> LENGTH: 9
<212> TYPE: PRT
<213> ORGANISM: Artificial Sequence
<220> FEATURE:
<223> OTHER INFORMATION: PRAME p301-9I

<400> SEQUENCE: 30

Leu Tyr Val Asp Ser Leu Phe Phe Ile
1               5

<210> SEQ ID NO 31
<211> LENGTH: 9
<212> TYPE: PRT
<213> ORGANISM: Artificial Sequence
<220> FEATURE:
<223> OTHER INFORMATION: sequence motif for risk search
<220> FEATURE:
<221> NAME/KEY: MISC_FEATURE
<222> LOCATION: (1)..(1)
<223> OTHER INFORMATION: Xaa at position 1 can be any amino acid.
<220> FEATURE:
<221> NAME/KEY: MISC_FEATURE
<222> LOCATION: (5)..(5)
<223> OTHER INFORMATION: Xaa at position 5 can be any amino acid.

<400> SEQUENCE: 31

Xaa Tyr Val Asp Xaa Leu Phe Phe Leu
1               5

<210> SEQ ID NO 32
<211> LENGTH: 9
<212> TYPE: PRT
<213> ORGANISM: Artificial Sequence
<220> FEATURE:
<223> OTHER INFORMATION: sequence motif for risk search
<220> FEATURE:
<221> NAME/KEY: MISC_FEATURE
<222> LOCATION: (1)..(1)
<223> OTHER INFORMATION: Xaa at position 1 can be any amino acid.
<220> FEATURE:
<221> NAME/KEY: MISC_FEATURE
<222> LOCATION: (5)..(5)
<223> OTHER INFORMATION: Xaa at position 5 can be any amino acid.

<400> SEQUENCE: 32

Xaa Tyr Val Asp Xaa Leu Phe Phe Phe
1               5

<210> SEQ ID NO 33
<211> LENGTH: 9
<212> TYPE: PRT
<213> ORGANISM: Artificial Sequence
<220> FEATURE:
<223> OTHER INFORMATION: sequence motif for risk search
<220> FEATURE:
<221> NAME/KEY: MISC_FEATURE
<222> LOCATION: (1)..(1)
<223> OTHER INFORMATION: Xaa at position 1 can be any amino acid.
<220> FEATURE:
<221> NAME/KEY: MISC_FEATURE
<222> LOCATION: (5)..(5)
<223> OTHER INFORMATION: Xaa at position 5 can be any amino acid.

<400> SEQUENCE: 33

Xaa Tyr Val Asp Xaa Leu Phe Phe Ile
1               5

<210> SEQ ID NO 34
<211> LENGTH: 9
<212> TYPE: PRT
<213> ORGANISM: Artificial Sequence
<220> FEATURE:
<223> OTHER INFORMATION: F-box only protein 24 isoform 3

<400> SEQUENCE: 34

Asp Tyr Val Gly Thr Leu Phe Phe Leu
1               5

<210> SEQ ID NO 35
<211> LENGTH: 9
<212> TYPE: PRT

<213> ORGANISM: Artificial Sequence
<220> FEATURE:
<223> OTHER INFORMATION: pre-mRNA-processing factor 40 homolog A isoform
X5

<400> SEQUENCE: 35

Ile Tyr Glu Asp Val Leu Phe Phe Leu
1 5

<210> SEQ ID NO 36
<211> LENGTH: 9
<212> TYPE: PRT
<213> ORGANISM: Artificial Sequence
<220> FEATURE:
<223> OTHER INFORMATION: pre-mRNA-processing factor 40 homolog B

<400> SEQUENCE: 36

Val Tyr Asp Asp Val Leu Phe Phe Leu
1 5

<210> SEQ ID NO 37
<211> LENGTH: 9
<212> TYPE: PRT
<213> ORGANISM: Artificial Sequence
<220> FEATURE:
<223> OTHER INFORMATION: cytoskelton associated protein 5

<400> SEQUENCE: 37

Leu Tyr Val Asp Leu Leu Phe Phe Pro
1 5

<210> SEQ ID NO 38
<211> LENGTH: 9
<212> TYPE: PRT
<213> ORGANISM: Artificial Sequence
<220> FEATURE:
<223> OTHER INFORMATION: potassium channel subfamily K member 12

<400> SEQUENCE: 38

Asp Tyr Val Asp Ser Leu Tyr Phe Cys
1 5

<210> SEQ ID NO 39
<211> LENGTH: 9
<212> TYPE: PRT
<213> ORGANISM: Artificial Sequence
<220> FEATURE:
<223> OTHER INFORMATION: DENN domain-containing protein 4B isoform 2

<400> SEQUENCE: 39

Arg Asp Val Asp Asn Leu Phe Phe Leu
1 5

<210> SEQ ID NO 40
<211> LENGTH: 9
<212> TYPE: PRT
<213> ORGANISM: Artificial Sequence
<220> FEATURE:
<223> OTHER INFORMATION: CSGIcA-T protein

<400> SEQUENCE: 40

His Pro Val Asp Thr Leu Phe Phe Leu
1 5

PRAME BINDING MOLECULE

CROSS-REFERENCE TO RELATED APPLICATIONS

This application is a national stage application of PCT/JP2021/044807 filed 7 Dec. 2021 which claims priority to Japanese Patent Application No. 2020-205384 filed 10 Dec. 2020. The entire disclosures of each application are herein incorporated by reference.

SEQUENCE LISTING

The instant application contains a Sequence Listing which has been submitted electronically in ASCII format and is hereby incorporated by reference in its entirety. Said ASCII copy, created on 1 Jun. 2026, is named ReplacementSequenceListing0223-0114-PCT-US.txt and is 11,064 bytes in size.

TECHNICAL FIELD

The present invention relates to a PRAME-binding molecule and the like.

BACKGROUND ART

Preferentially expressed antigen in melanoma (PRAME) is known to be a cancer-testis antigen and is only slightly expressed in normal adult tissues in the endometrium, ovary, and adrenal glands, in addition to the testis. Known cancers with high expression of PRAME include melanoma (95% of patients), lung cancer (50%), breast cancer (27%), acute leukemia (30%), and multiple myeloma (52%) (Non-patent Literature (NPL) 1, 2, and 3), and PRAME is attracting attention as a target for cancer treatment. The peptides that are known to be used as the target include p100-108, p142-151, p300-309, p425-433, p435-443, and the like for HLA-A2, and p301-309 for HLA-A24. T cells that recognize pMHC have been cloned, T-cell receptors (TCRs) have been isolated, and their functions have been analyzed (NPL 4, 5, and 6). However, so far no TCR that can be used for cancer treatment has been isolated.

CITATION LIST

Non-Patent Literature

NPL 1: N. van Baren, H. Chambost, A. Ferrant, L. Michaux, H. Ikeda, I. Millard, D. Olive, T. Boon, P. G. Coulie (1998), PRAME, a gene encoding an antigen recognized on a human melanoma by cytolytic T cells, is expressed in acute leukaemia cells. Br. J. Haematol. 102:1376-1379.

NPL 2: E. Neumann, A. Engelsberg, J. Decker, S. Storkel, E. Jaeger, C. Huber, B. Seliger (1998), Heterogeneous expression of the tumor-associated antigens RAGE-1, PRAME, and glycoprotein 75 in human renal cell carcinoma candidates for T-cell-based immunotherapies? Cancer Res. 58:4090-4095.

NPL 3: C. Pellat-Deceunynck, M. P. Mellerin, N. Labarriere, G. Jego, A. Moreau-Aubry, J. L. Harousseau, F. Jotereau, R. Bataille (2000), The cancer germ-line genes MAGE-1, MAGE-3 and PRAME are commonly expressed by human myeloma cells. Eur. J. Immunol. 30:803-809.

NPL 4: Jan H. Kessler, Nico J. Beekman, Sandra A. Bres-Vloemans, Pauline Verdijk, Peter A. van Veelen, Antoinette M. Kloosterman-Joosten, Debby C. J. Vissers, George J. A. ten Bosch, Michel G. D. Kester, Alice Sijts, Jan Wouter Drijfhout, Ferry Ossendorp, Rienk Offringa, Cornelis J. M. Melief (2001), Efficient Identification of Novel Hla-A*0201-Presented Cytotoxic T Lymphocyte Epitopes in the Widely Expressed Tumor Antigen Prame by Proteasome-Mediated Digestion Analysis, JEM, 193 (1).

NPL 5: Concetta Quintarelli, Gianpietro Dotti, Sayyeda T. Hasan, Biagio De Angelis, Valentina Hoyos, Santa Errichiello, Martha Mims, Luigia Luciano, Jessica Shafer, Ann M. Leen, Helen E. Heslop, Cliona M. Rooney, Fabrizio Pane, Malcolm K. Brenner, and Barbara Savoldo (2011), High-avidity cytotoxic T lymphocytes specific for a new PRAME-derived peptide can target leukemic and leukemic precursor cells, Blood vol. 117 (12), 3353-3362.

NPL 6: Hideyuki Ikeda, Bernard Lethe, Frederic Lehmann, Nicolas Van Baren, Jean-Francois Baurain, Charles De Smet, Hervé Chambost, Massimo Vitale, Alessandro Moretta, Thierry Boon (1997), Characterization of an Antigen That is Recognized on a Melanoma Showing Partial HLA Loss by CTL Expressing an NK Inhibitory Receptor, Immunity, vol. 6, 199-208.

NPL 7: Yasushi Akahori, Linan Wang, Motohiro Yoneyama, Naohiro Seo, Satoshi Okumura, Yoshihiro Miyahara, Yasunori Amaishi, Sachiko Okamoto, Junichi Mineno, Hiroaki Ikeda, Takehiro Maki, Hiroshi Fujiwara, Yoshiki Akatsuka, Takuma Kato, and Hiroshi Shiku, 2018, Antitumor activity of CAR-T cells targeting the intracellular oncoprotein WT1 can be enhanced by vaccination, Blood, 132 (11), 1134-1145.

NPL 8: Yasushi Akahori, Gene Kurosawa, Mariko Sumitomo, Miwa Morita, Chiho Muramatsu, Keiko Eguchi, Miho Tanaka, Kazuhiro Suzuki, Mototaka Sugiura, Yoshitaka Iba, Atsushi Sugioka, Yoshikazu Kurosawa (2008), Isolation of antigen/antibody complexes through organic solvent (ICOS) method, Biochemical and Biophysical Research Communications, 11, 129.

SUMMARY OF INVENTION

Technical Problem

An object of the present invention is to provide a PRAME-binding molecule.

Solution to Problem

In view of the problem above, the present inventors attempted isolation of an antibody that recognizes an HLA-A24 PRAMEp301-309 pMHC complex and production of a CAR using the complex. As a result of further research, the inventors found that the problem can be solved by a PRAME-binding molecule that comprises a heavy-chain variable region containing a heavy-chain CDR1 comprising the amino acid sequence represented by SEQ ID NO: 1, a heavy-chain CDR2 comprising the amino acid sequence represented by SEQ ID NO: 2, and a heavy-chain CDR3 comprising the amino acid sequence represented by SEQ ID NO: 3, and/or a light-chain variable region containing a light-chain CDR1 comprising the amino acid sequence represented by SEQ ID NO: 9, a light-chain CDR2 comprising the amino acid sequence represented by SEQ ID NO: 10, and a light-chain CDR3 comprising the amino acid sequence represented by SEQ ID NO: 11. The inventors conducted further research on the basis of this finding and completed the present invention. Specifically, the present invention includes the following subject matter.

Item 1.

A PRAME-binding molecule comprising a heavy-chain variable region containing a heavy-chain CDR1 comprising the amino acid sequence represented by SEQ ID NO: 1, a heavy-chain CDR2 comprising the amino acid sequence represented by SEQ ID NO: 2, and a heavy-chain CDR3 comprising the amino acid sequence represented by SEQ ID NO: 3, and/or a light-chain variable region containing a light-chain CDR1 comprising the amino acid sequence represented by SEQ ID NO: 9, a light-chain CDR2 comprising the amino acid sequence represented by SEQ ID NO: 10, and a light-chain CDR3 comprising the amino acid sequence represented by SEQ ID NO: 11.

Item 2.

The PRAME-binding molecule according to Item 1, comprising the heavy-chain variable region and the light-chain variable region.

Item 3.

The PRAME-binding molecule according to Item 1 or 2, which has binding capability to an HLA-A24 PRAMEp301-309 pMHC complex.

Item 4.

The PRAME-binding molecule according to any one of Items 1 to 3, wherein the binding capability of the PRAME-binding molecule to a peptide consisting of the amino acid sequence represented by SEQ ID NO: 19, a peptide consisting of the amino acid sequence represented by SEQ ID NO: 20, a peptide consisting of the amino acid sequence represented by SEQ ID NO: 21, a peptide consisting of the amino acid sequence represented by SEQ ID NO: 23, a peptide consisting of the amino acid sequence represented by SEQ ID NO: 24, a peptide consisting of the amino acid sequence represented by SEQ ID NO: 25, or a peptide consisting of the amino acid sequence represented by SEQ ID NO: 26 is equal to or less than ½ of the binding capability of the PRAME-binding molecule to a peptide consisting of the amino acid sequence represented by SEQ ID NO: 17.

Item 5.

The PRAME-binding molecule according to any one of Items 1 to 4, which is a chimeric antigen receptor.

Item 6.

The PRAME-binding molecule according to Item 5, comprising a core domain containing an scFv domain that contains the heavy-chain variable region and the light-chain variable region, a transmembrane domain, and an intracellular domain of TCR.

Item 7.

The PRAME-binding molecule according to Item 6, wherein the core domain further contains an intracellular domain of a co-stimulator.

Item 8.

The PRAME-binding molecule according to any one of Items 1 to 4, which is an antibody.

Item 9.

A polynucleotide encoding the PRAME-binding molecule according to any one of Items 1 to 8.

Item 10.

A cell comprising the polynucleotide according to Item 9.

Item 11.

A lymphocyte cell comprising a polynucleotide encoding the PRAME-binding molecule according to any one of Items 5 to 7.

Item 12.

A pharmaceutical composition comprising the lymphocyte cell according to Item 11 or the PRAME-binding molecule according to Item 8.

Item 13.

The pharmaceutical composition according to Item 12, which is for use in the diagnosis, treatment, or prevention of cancer.

Advantageous Effects of Invention

The present invention provides a PRAME-binding molecule. The PRAME-binding molecule of the present invention has specific CDR sequences. Thus, the PRAME-binding molecule of the present invention has excellent binding capability to PRAME and also has an excellent anticancer effect particularly when used as a chimeric antigen receptor.

DESCRIPTION OF EMBODIMENTS

1. Definition

Figure 1A:
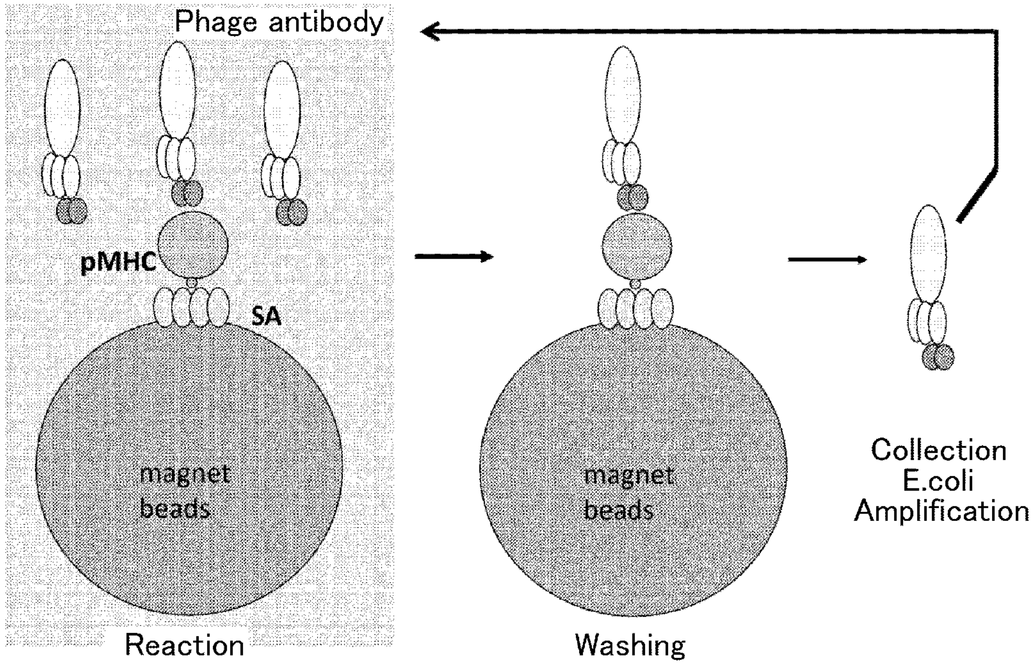
FIG. 1*a* is a schematic view of an antibody library screen method (magnetic bead screen method) (Test Example 1). Artificially generated HLA-A24 PRAMEp301-309 was bound to Dynabeads MyOne Streptavidin T1 (Invitrogen) and reacted with a human antibody library, and antibody clones were concentrated.

In the present specification, the terms "comprising," "containing," and "including" include the concepts of comprising, containing, consisting essentially of, and consisting of.

The "identity" of amino acid sequences refers to the degree to which two or more contrastable amino acid sequences match each other. Thus, the higher the degree of match between two amino acid sequences, the higher the identity or similarity of those sequences. The level of amino acid sequence identity is determined, for example, by using FASTA (a tool for sequence analysis) with default parameters. Alternatively, the level of amino acid sequence identity can be determined by using the BLAST algorithm by Karlin and Altschul (Karlin S, Altschul SF. Methods for assessing the statistical significance of molecular sequence features by using general scoring schemes, Proc Natl Acad Sci USA. 87:2264-2268 (1990), Karlin S, Altschul SF. Applications and statistics for multiple high-scoring segments in molecular sequences, Proc Natl Acad Sci USA. 90:5873-7 (1993)). A program called "BLASTX," based on this BLAST algorithm, has been developed. The specific techniques of these analysis methods are known and can be found on the website of the National Center of Biotechnology Information (NCBI) (www.ncbi.nlm.nih.gov). The "identity" of base sequences is also defined in the same manner as above.

In the present specification, "conservative substitution" means the substitution of an amino acid residue with an amino acid residue having a similar side chain. For example, the substitution between amino acid residues having a basic side chain such as lysine, arginine, and histidine is considered to be a conservative substitution. The following substitutions between other amino acid residues are also considered to be a conservative substitution: the substitution between amino acid residues having an acidic side chain, such as aspartic acid and glutamic acid; the substitution between amino acid residues having an uncharged polar side chain, such as glycine, asparagine, glutamine, serine, threonine, tyrosine, and cysteine; the substitution between amino acid residues having a nonpolar side chain, such as alanine, valine, leucine, isoleucine, proline, phenylalanine, methionine, and tryptophan; the substitution between amino acid residues having a beta-branched side chain, such as threonine, valine, and isoleucine; and the substitution between amino acid residues having an aromatic side chain, such as tyrosine, phenylalanine, tryptophan, and histidine.

In the present specification, "CDR" is an abbreviation for complementarity determining region. CDR is a region in the variable regions of immunoglobulins and is deeply involved in the specific binding of an antibody to its antigen. The phrase "light-chain CDR" refers to a CDR present in the light-chain variable regions of immunoglobulins, and the phrase "heavy-chain CDR" refers to a CDR present in the heavy-chain variable regions of immunoglobulins.

In the present specification, the phrase "variable region" refers to a region containing CDR1 to CDR3 (simply "CDRs 1-3" below). The order in which these CDRs 1-3 are arranged is not limited; however, the variable region preferably refers to a region in which CDR1, CDR2, and CDR3 are arranged in this order in the direction from the N-terminus toward the C-terminus or in the reverse order either consecutively or via other amino acid sequences referred to as "framework regions" (FRs), which are described later. The phrase "heavy-chain variable region" refers to a region in which heavy-chain CDRs 1-3 are arranged, and the phrase "light-chain variable region" refers to a region in which light-chain CDRs 1-3 are arranged.

The regions other than CDRs 1-3 of each variable region are referred to as "framework regions" (FRs), as mentioned above. In particular, the region between the N-terminus and CDR1 of a variable region is defined as FR1, the region between CDR1 and CDR2 as FR2, the region between CDR2 and CDR3 as FR3, and the region between CDR3 and the C-terminus of a variable region as FR4.

2. PRAME-Binding Molecule

In an embodiment, the present invention relates to a PRAME-binding molecule comprising a heavy-chain variable region containing a heavy-chain CDR1 comprising the amino acid sequence represented by SEQ ID NO: 1, a heavy-chain CDR2 comprising the amino acid sequence represented by SEQ ID NO: 2, and a heavy-chain CDR3 comprising the amino acid sequence represented by SEQ ID NO: 3; and/or a light-chain variable region containing a light-chain CDR1 comprising the amino acid sequence represented by SEQ ID NO: 9, a light-chain CDR2 comprising the amino acid sequence represented by SEQ ID NO: 10, and a light-chain CDR3 comprising the amino acid sequence represented by SEQ ID NO: 11 (which may be referred to as "the PRAME-binding molecule of the present invention" in the present specification). The PRAME-binding molecule of the present invention is described below.

The PRAME-binding molecule of the present invention can be any PRAME-binding molecule as long as the PRAME-binding molecule comprises a heavy-chain variable region containing a heavy-chain CDR1 comprising the amino acid sequence represented by SEQ ID NO: 1, a heavy-chain CDR2 comprising the amino acid sequence represented by SEQ ID NO: 2, and a heavy-chain CDR3 comprising the amino acid sequence represented by SEQ ID NO: 3, and/or a light-chain variable region containing a light-chain CDR1 comprising the amino acid sequence represented by SEQ ID NO: 9, a light-chain CDR2 comprising the amino acid sequence represented by SEQ ID NO: 10, and a light-chain CDR3 comprising the amino acid sequence represented by SEQ ID NO: 11, and as long as the PRAME-binding molecule is capable of binding to PRAME.

The PRAME-binding molecule of the present invention may be a molecule formed of a single type of polypeptide or a molecule formed of a complex of two or more types of polypeptides. The PRAME-binding molecule of the present invention may also be a molecule formed of a polypeptide or of a complex of polypeptides, or a molecule formed of a polypeptide or complex of polypeptides to which another substance (e.g., a fluorescent substance, a radioactive substance, or an inorganic particle) is linked.

The binding capability to PRAME can be measured in accordance with a known method, such as by ELISA (specifically, for example, by the method of Test Example 2). The binding capability of the PRAME-binding molecule of the present invention to PRAME is, for example, at least 20%, at least 50%, at least 70%, at least 80%, at least 90%, at least 95%, or at least 99% of the binding capability of #98 antibody to PRAME in the Examples described later, which is taken as 100%.

The PRAME-binding molecule of the present invention preferably contains both the heavy-chain variable region and the light-chain variable region.

The heavy-chain variable region is preferably a heavy-chain variable region comprising the amino acid sequence represented by SEQ ID NO: 4, or an amino acid sequence having at least 90% (preferably at least 95%, preferably at least 98%, preferably at least 99%) identity with the amino acid sequence represented by SEQ ID NO: 4. The light-chain variable region is preferably a light-chain variable region comprising the amino acid sequence represented by SEQ ID NO: 12, or an amino acid sequence having at least 90% (preferably at least 95%, preferably at least 98%, preferably at least 99%) identity with the amino acid sequence represented by SEQ ID NO: 12. If the amino acid sequence of SEQ ID NO: 4 or 12 is mutated, the mutation is preferably a substitution of an amino acid, and more preferably a conservative substitution of an amino acid.

The PRAME-binding molecule of the present invention can have binding capability to a HLA-A24 PRAMEp301-309 pMHC complex. The HLA-A24 PRAMEp301-309 pMHC complex is a complex of HLA-A24 and a partial peptide of PRAME (p301-309: SEQ ID NO: 17). The embodiment of the complex is not particularly limited as long as HLA presents the peptide as an antigen.

The PRAME-binding molecule of the present invention can specifically recognize PRAMEp301-309 (SEQ ID NO: 17). From this viewpoint, the binding capability of the PRAME-binding molecule of the present invention to at least one member selected from the group consisting of peptides in which part of PRAMEp301-309 is mutated (a peptide consisting of the amino acid sequence represented by SEQ ID NO: 19, a peptide consisting of the amino acid sequence represented by SEQ ID NO: 20, a peptide consisting of the amino acid sequence represented by SEQ ID NO: 21, a peptide consisting of the amino acid sequence represented by SEQ ID NO: 23, a peptide consisting of the amino acid sequence represented by SEQ ID NO: 24, a peptide consisting of the amino acid sequence represented by SEQ ID NO: 25, and a peptide consisting of the amino acid sequence represented by SEQ ID NO: 26) (preferably, two members or more, three members or more, four members or more, five members or more, six members or more, or seven members (all)), is preferably ½ or less (preferably, ⅕ or less, 1/10 or less, 1/20 or less, 1/100 or less, 1/500 or less, 1/2000 or less, or 1/10000 or less) of the binding capability of the PRAME-binding molecule of the present invention to PRAMEp301-309 (SEQ ID NO: 17).

The PRAME-binding molecule of the present invention may be chemically modified. The polypeptide that constitutes the PRAME-binding molecule of the present invention may have a carboxyl group (—COOH), carboxylate (—COO—), amide (—$CONH_2$), or ester (—COOR) at the C-terminus. "R" in the ester is, for example, a $C_{1-6}$ alkyl group, such as methyl, ethyl, n-propyl, isopropyl, or n-butyl; a $C_{3-8}$ cycloalkyl group, such as cyclopentyl or cyclohexyl;

a $C_{6-12}$ aryl group, such as phenyl or α-naphthyl; a phenyl-$C_{1-2}$ alkyl group, such as benzyl or phenethyl; a $C_{7-14}$ aralkyl group, such as an α-naphthyl-$C_{1-2}$ alkyl group, such as α-naphthyl methyl; or a pivaloyloxymethyl group. The polypeptide that constitutes the PRAME-binding molecule of the present invention may have an amidated or esterified carboxyl group (or carboxylate), which is not the carboxyl group at the C-terminus. The ester in this case may be, for example, the esters of the C-terminus described above. The polypeptide that constitutes the PRAME-binding molecule of the present invention includes polypeptides having the amino group of the N-terminal amino acid residue protected by a protective group (e.g., a $C_{1-6}$ acyl group, including a $C_{1-6}$ alkanoyl, such as a formyl group and an acetyl group), polypeptides having the N-terminal glutamine residue pyroglutamated that can be formed due to cleavage in vivo; and polypeptides having a substituent (e.g., —OH, —SH, an amino group, an imidazole group, an indole group, and a guanidino group) on a side chain of an amino acid in the molecule protected by an appropriate protective group (e.g., a $C_{1-6}$ acyl group, including a $C_{1-6}$ alkanoyl group, such as a formyl group and an acetyl group).

The PRAME-binding molecule of the present invention may have a protein or peptide (e.g., a known protein tag or signal sequence) added. Examples of protein tags include biotin, a His tag, a FLAG tag, a Halo tag, a MBP tag, a HA tag, a Myc tag, a V5 tag, a PA tag, and a fluorescent protein tag.

The PRAME-binding molecule of the present invention may be a pharmaceutically acceptable salt formed with an acid or base. The salt can be any pharmaceutically acceptable salt, and can be either an acid salt or a basic salt. Examples of acid salts include inorganic acid salts, such as hydrochloride, hydrobromide, sulfate, nitrate, and phosphate; organic acid salts, such as acetate, propionate, tartrate, fumarate, maleate, malate, citrate, methanesulfonate, and para-toluenesulfonate; and amino acid salts, such as aspartate and glutamate. Examples of basic salts include alkali metal salts, such as sodium salts and potassium salts; and alkaline-earth metal salts, such as calcium salts and magnesium salts.

The PRAME-binding molecule of the present invention may be in the form of a solvate. The solvent can be any pharmaceutically acceptable solvent, and may be, for example, water, ethanol, glycerol, or acetic acid.

2-1. Antibody

In a preferable embodiment, the PRAME-binding molecule of the present invention is an antibody (in the present specification, the PRAME-binding molecule of the present invention being an antibody may be referred to as "the antibody of the present invention").

The antibody of the present invention is a monoclonal antibody.

The antibody of the present invention can be of any molecular weight. The lower limit is, for example, 20,000, preferably 50,000, preferably 100,000, and more preferably 120,000. The upper limit is, for example, 1,000,000, preferably 500,000, and more preferably 200,000.

The antibody of the present invention may be of any structure. The antibody of the present invention may contain constant regions or no constant region. If the antibody of the present invention contains constant regions, the antibody of the present invention may contain all of the constant regions of the heavy chain (CH1, CH2, and CH3) and the constant regions of the light chain (CL), or any one or a combination of two or more constant regions of these constant regions.

Specific examples of the structure of the antibody of the present invention include immunoglobulins, Fab, $F(ab')_2$, minibody, SCFV Fc, Fv, scFv, diabody, triabody, and tetrabody. Of these, an immunoglobulin is preferable from the standpoint of the effect of the present invention.

An immunoglobulin has a structure formed of a combination of two structures each of which is composed of a single heavy chain that contains a heavy-chain variable region and a heavy-chain constant region and a single light chain that contains a light-chain variable region and a light-chain constant region.

"Fab" contains a fragment of a heavy chain containing the heavy-chain variable region and CH1 in the heavy-chain constant region and a light chain containing the light-chain variable region and the light-chain constant region (CL), with the heavy-chain variable region and the light-chain variable region being aggregated by non-covalent intermolecular interaction described above, or bound to each other through a disulfide bond. In Fab, CH1 and CL may be linked through a disulfide bond between the thiol groups of the cysteine residues present in CH1 and CL.

"$F(ab')_2$" contains two pairs of Fabs, with CH1 of one Fab linked with CH1 of the other Fab through a disulfide bond between the thiol groups of their cysteine residues.

"Minibody" refers to the structure in which two fragments each containing CH3 bound to a heavy-chain variable region constituting scFV, described below, are aggregated between CH3 and CH3 by non-covalent intermolecular interaction.

"scFv-Fc" refers to the structure in which two antibody fragments each containing scFv, CH2, and CH3 are aggregated between CH3 and CH3 by non-covalent intermolecular interaction, as with the minibody, and the fragments are linked through a disulfide bond between thiol groups of the cysteine residues contained in each CH3.

"Fv" is considered to be the smallest structural unit of an antibody with the heavy-chain variable region and the light-chain variable region being aggregated by non-covalent intermolecular interaction. In Fv, the thiol group of the cysteine residue present in the heavy-chain variable region may be linked to the thiol group of the cysteine residue present in the light-chain variable region through a disulfide bond.

"scFv" has the structure in which the C-terminus of the heavy-chain variable region and the N-terminus of the light-chain variable region are bound through a linker, or the N-terminus of the heavy-chain variable region and the C-terminus of the light-chain variable region are bound through a linker, and is also referred to as a "single-chain antibody."

The "diabody," "triabody," and "tetrabody" respectively refer to a dimer, a trimer, and a tetramer formed by scFv described above and are each aggregated and structurally stabilized, for example, by non-covalent intermolecular interaction of the variable regions, as with Fv.

If the antibody of the present invention is an immunoglobulin, its class is not particularly limited. The classes include, for example, IgA, IgD, IgE, IgG, and IgM, as well as subclasses of these classes. The class of the antibody of the present invention is, for example, IgG or IgM, preferably IgG, and more preferably IgG1.

The origin of the antibody of the present invention is not particularly limited. The antibody of the present invention may be, for example, a human-derived antibody, a mouse-derived antibody, a rat-derived antibody, a rabbit-derived antibody, a monkey-derived antibody, or a chimpanzee-derived antibody. The antibody of the present invention may be a chimeric antibody (e.g., an antibody formed by replacing the amino acid sequence of the constant region of an antibody derived from a non-human organism (e.g., a mouse) with the amino acid sequence of the constant region of a human-derived antibody), a humanized antibody, or a fully humanized antibody.

The antibody of the present invention can be produced, for example, by a method including culturing a host transformed with a polynucleotide encoding the antibody of the present invention, and collecting the fraction containing the antibody of the present invention.

The polynucleotide encoding the antibody of the present invention can be any polynucleotide that expressibly contains the sequence of the antibody of the present invention, and may contain other sequences in addition to the coding sequence of the antibody of the present invention. Other sequences include a secretory-signal-peptide-coding sequence, a promoter sequence, an enhancer sequence, a repressor sequence, an insulator sequence, an origin of replication, and a drug-resistant-gene-coding sequence that are located adjacent to the coding sequence of the antibody of the present invention. The polynucleotide encoding the antibody of the present invention may also be a linear polynucleotide or a cyclic polynucleotide (e.g., a vector).

Specific examples of polynucleotides include (I) polynucleotides containing a base sequence encoding at least one member selected from the group consisting of the heavy chain, the heavy-chain variable region, the heavy-chain CDR1, the heavy-chain CDR2, and the heavy-chain CDR3 of the antibody of the present invention, (II) polynucleotides containing a base sequence encoding at least one member selected from the group consisting of the light chain, the light-chain variable region, the light-chain CDR1, the light-chain CDR2, and the light-chain CDR3 of the antibody of the present invention, and (III) polynucleotides containing a base sequence encoding at least one member selected from the group consisting of the heavy chain, the heavy-chain variable region, the heavy-chain CDR1, the heavy-chain CDR2, and the heavy-chain CDR3 of the antibody of the present invention, and polynucleotides containing a base sequence encoding at least one member selected from the group consisting of the light chain, the light-chain variable region, the light-chain CDR1, the light-chain CDR2, and the light-chain CDR3 of the antibody of the present invention.

The host can be any organism, and is, for example, insect cells, eukaryotic cells, or mammal cells. Of these, mammal cells, such as HEK cells, CHO cells, NSO cells, SP2/0 cells, or P3U1 cells, are preferable from the standpoint of more efficiently expressing the antibody. The methods for transformation, culture, and collection are not particularly limited, and any method known in the field of antibody production can be used. After being collected, the antibody of the present invention may optionally be purified. Purification can be performed by a method known in the field of antibody production, such as chromatography or dialysis.

2-2. Chimeric Antigen Receptor

In a preferable embodiment, the PRAME-binding molecule of the present invention is a chimeric antigen receptor. (In the present specification, the PRAME-binding molecule of the present invention being a chimeric antigen receptor may be referred to as "the chimeric antigen receptor of the present invention.")

The chimeric antigen receptor (CAR) is typically a chimeric protein that has its single-chain antibody (ScFv) composed of a light chain (VL) bound in tandem to a heavy chain (VH) of the variable region of a monoclonal antibody at a position closer to the N-terminus as a domain responsible for its binding capability to an antigen and its T-cell receptor (TCR) Z chain at a position closer to the C-terminus. T cells expressing CAR are referred to as "CAR-T cells."

The domain responsible for the binding capability to an antigen (PRAME) (PRAME-binding domain) in the chimeric antigen receptor of the present invention is not particularly limited as long as the domain contains a heavy-chain variable region containing a heavy-chain CDR1 comprising the amino acid sequence represented by SEQ ID NO: 1, a heavy-chain CDR2 comprising the amino acid sequence represented by SEQ ID NO: 2, and a heavy-chain CDR3 comprising the amino acid sequence represented by SEQ ID NO: 3, and/or a light-chain variable region containing a light-chain CDR1 comprising the amino acid sequence represented by SEQ ID NO: 9, a light-chain CDR2 comprising the amino acid sequence represented by SEQ ID NO: 10, and a light-chain CDR3 comprising the amino acid sequence represented by SEQ ID NO: 11.

The PRAME-binding domain preferably has the structure of scFv. The linker that links the heavy-chain variable region with the light-chain variable region can be any linker that maintains functionality of the chimeric antigen receptor. The linker is preferably, for example, a linker composed of glycine alone or glycine and serine. The number of amino acid residues of the linker is, for example, 5 to 30, preferably 10 to 20, and more preferably 15.

The chimeric antigen receptor of the present invention typically contains a core domain containing an scFv domain having a heavy-chain variable region and a light-chain variable region, a transmembrane domain, and the intracellular domain of TCR. In general, in the core domain, the scFv domain, the transmembrane domain, and the intracellular domain of TCR are arranged in this order from the N-terminus directly or via other domains.

The transmembrane domain can be of any type that does not interfere with the functionality of the chimeric antigen receptor. For example, CD28, CD3zeta, CD4, or CD8alpha, which are expressed in cells such as T cells, can be used. These transmembrane domains may be mutated as long as the functionality of the chimeric antigen receptor is not interfered with.

The intracellular domain of TCR can be, for example, an intracellular domain derived from CD3, which is also called a "TCRZ chain." CD3 may be mutated as long as the functionality of the chimeric antigen receptor is not interfered with. Mutation of CD3 is preferably made such that CD3 contains ITAM (immunoreceptor tyrosine-based activation motif).

The chimeric antigen receptor of the present invention preferably has a spacer sequence between the scFv domain and the transmembrane domain. The spacer sequence can be of any length and can be formed of any amino acid residues as long as the functionality of the chimeric antigen receptor is not interfered with. For example, the spacer sequence can be designed so as to have about 10 to 200 amino acid residues. The spacer sequence for use is preferably the sequence of the constant region of the light chain.

The core domain in the chimeric antigen receptor of the present invention preferably further contains the intracellular domain of a co-stimulator. The intracellular domain of a co-stimulator can be of any intracellular domain derived from a co-stimulator of cells such as T cells. For example, at least one member selected from the group consisting of Ox40, 4-1BB, GITR, CD27, CD278, CD28, and the like can be suitably selected and used. The intracellular domain of these co-stimulators may be mutated as long as the functionality of the chimeric antigen receptor is not interfered with. The position of the intracellular domain of a co-stimulator is not particularly limited as long as the intracellular domain is at a position closer to the C-terminus of the transmembrane domain; the intracellular domain may be on the cell membrane side of the intracellular domain of TCR or on the side opposite to the cell membrane. In a preferable embodiment of the present invention, the intracellular domain of a co-stimulator is preferably placed on the side opposite to the cell membrane of the intracellular domain of TCR.

The chimeric antigen receptor of the present invention preferably contains a ligand domain, such as a GITRL domain, a 4-1BBL domain, or an ICOSL domain, at a position closer to the C-terminus of the core domain via a self-cleaving peptide domain. This can increase the expression efficiency of the chimeric antigen receptor or the cytotoxic activity of CAR-T cells containing the chimeric antigen receptor.

In the present specification, the phrase "self-cleaving peptide" refers to a peptide sequence with cleavage activity occurring between two amino acid residues in the peptide sequence. Examples of self-cleaving peptides include 2A peptides and 2A-like peptides. For example, in 2A peptides or 2A-like peptides, cleavage occurs between the glycine residue and the proline residue of these peptides. This occurs because of the "ribosomal skipping mechanism," in which a normal peptide linkage between the glycine residue and the proline residue does not form during translation, and this does not affect the translation downstream. The ribosomal skipping mechanism is known in the art and is used in the expression of multiple proteins encoded by a single molecular messenger RNA (mRNA). The self-cleaving peptide for use in the present invention can be obtained from 2A peptides of viruses or 2A-like peptides that have equivalent functionality. For example, the self-cleaving peptide can be selected from the group consisting of 2A peptides derived from foot-and-mouth disease virus (FMDV) (F2A), 2A peptides derived from equine rhinitis A virus (ERAV) (E2A), 2A peptides derived from porcine teschovirus (PTV-1) (P2A), and 2A peptides derived from Thosea asigna virus (TaV) (T2A). The self-cleaving peptide domain may be mutated as long as the activity of the self-cleaving peptide domain is not greatly impaired.

The techniques for producing a chimeric antigen receptor and a CAR-T cell that expresses the chimeric antigen receptor are known. Chimeric antigen receptors and CAR-T cells can be produced in accordance with a known method or an equivalent method.

3. Polynucleotide

In an embodiment, the present invention relates to a polynucleotide encoding the PRAME-binding molecule of the present invention (which may be referred to as "the polynucleotide of the present invention" in the present specification). The polynucleotide of the present invention is described below.

The polynucleotide of the present invention may contain other sequences in addition to the coding sequence of the PRAME-binding molecule of the present invention. Preferably, the polynucleotide of the present invention expressibly contains the sequence of the PRAME-binding molecule of the present invention. Other sequences include promoter sequences, enhancer sequences, repressor sequences, insulator sequences, origins of replication, reporter protein (e.g., fluorescent proteins) coding sequences, and drug-resistant-gene-coding sequences. The polynucleotide of the present invention may be a linear polynucleotide or a cyclic polynucleotide (e.g., a vector). The vector can be a plasmid vector or a virus vector (e.g., an adenovirus or retrovirus). The vector can also be, for example, a vector for cloning or for expression. The vector for expression includes vectors for prokaryotic cells, such as *Escherichia coli* or actinomycetes, and vectors for eukaryotic cells, such as yeast cells, insect cells, or mammal cells.

The polynucleotide of the present invention includes not only DNA and RNA but also known chemically modified DNA or RNA as described below. To prevent the degradation by hydrolases, such as nucleases, the phosphate residue (phosphate) of each nucleotide can be substituted with, for example, a chemically modified phosphate residue, such as phosphorothioate (PS), methylphosphonate, or phosphorodithionate. The hydroxyl group at position 2 of the ribose of each ribonucleotide may also be substituted with —OR (R represents, for example, CH3(2'-O-Me), $CH_2CH_2OCH_3$(2'-O-MOE), $CH_2CH_2NHC(NH)NH_2$, $CH_2CONHCH_3$, or $CH_2CH_2CN$). Additionally, the base moiety (pyrimidine, purine) may be chemically modified, by, for example, introduction of a methyl group or a cationic functional group into positon 5 of the pyrimidine base, or substitution of the carbonyl group at position 2 with thiocarbonyl. Additionally, the polynucleotide of the present invention also includes, but is not limited to, those formed by modifying the phosphate moiety or the hydroxyl portion, for example, by biotin, an amino group, a lower alkyl amine group, or an acetyl group. The term "polynucleotide" includes not only natural nucleic acids but also BNA (bridged nucleic acid), LNA (locked nucleic acid), and PNA (peptide nucleic acid).

4. Cell

In an embodiment, the present invention relates to a cell comprising the polynucleotide of the present invention (which may be referred to as "the cell of the present invention" in the present specification). The cell of the present invention is described below.

The cells from which the cell of the present invention is derived are not particularly limited. For the purpose of using the cell of the present invention in the production of the PRAME-binding molecule of the present invention, for example, cells that can be used for protein expression (e.g., insect cells, eukaryotic cells, mammal cells) can be used as the origin cells.

When the cell of the present invention comprises a polynucleotide encoding the chimeric antigen receptor of the present invention, the cell is preferably a lymphocyte cell (e.g., T cells (e.g., CD4-positive CD8-negative T cells, CD4-negative CD8-positive T cells, T cells prepared from iPS cells, αβ-T cells, and γδ-T cells), NK cells, and NKT cells). The lymphocyte cell is preferably a cell expressing the chimeric antigen receptor of the present invention. In a more specific embodiment of the lymphocyte cell of the present invention, the chimeric antigen receptor of the present invention is expressed on the cell membrane, and preferably expressed in such a state that the PRAME-binding domain is exposed outside the cell membrane.

A lymphocyte cell or the like expressing the chimeric antigen receptor recognizes PRAME in the PRAME-binding domain, and then intracellularly transfers a recognition signal to activate a signal that induces cytotoxic activity. In conjunction with this, the cell can mount attacks against other cells or tissues expressing PRAME, or exert cytotoxic activity.

When a cell exhibiting such a function is a CTL, this cell is called a "chimeric antigen receptor T-cell" ("CAR-T cell"). Cells that have potential to exhibit cytotoxic activity, such as NK cells, can also exert cytotoxic activity when the PRAME-binding domain binds to PRAME, as with the chimeric antigen receptor T-cell. Thus, a host cell comprising the polynucleotide encoding the chimeric antigen receptor (in particular, a host cell having cytotoxic activity) is useful as an active ingredient of pharmaceutical compositions.

Such lymphocyte cells or the like are useful for treatment or prevention of cancer or the like because they specifically recognize cancer tissue (tumor tissue). The type of cancer is not particularly limited, and includes blood cancer and solid cancer. Examples of blood cancer include various B-cell malignant lymphomas (B-cell acute lymphocytic leukemia, follicular lymphoma, diffuse lymphoma, mantle cell lymphoma, MALT lymphoma, intravascular B-cell lymphoma, CD20-positive Hodgkin's lymphoma), myeloproliferative diseases, myelodysplastic/myeloproliferative tumors (CMML, JMML, CML, MDS/MPN-UC), myelodysplastic syndrome, acute myeloid leukemia, multiple myeloma, and the like. Examples of solid cancer include lung cancer, colorectal cancer, ovarian cancer, breast cancer, brain tumor, stomach cancer, liver cancer, tongue cancer, thyroid cancer, kidney cancer, prostate cancer, uterine cancer, osteosarcoma, chondrosarcoma, rhabdomyosarcoma, melanoma, neuroblastoma, bladder cancer, and the like.

The cell of the present invention can be obtained by introducing the polynucleotide of the present invention into cells. If necessary, the cell containing the polynucleotide of the present invention may be concentrated, or may be concentrated using a specific marker (CD antigen, such as CD8) as an indicator.

5. Pharmaceutical Composition

In an embodiment, the present invention relates to a pharmaceutical composition comprising the lymphocyte cell containing the polynucleotide encoding the chimeric antigen receptor of the present invention or comprising the antibody of the present invention (which may be referred to as "the pharmaceutical composition of the present invention" in the present specification). The pharmaceutical composition of the present invention is described below.

The content of the cell or antibody in the pharmaceutical composition can be appropriately set in consideration of the type of target disease (e.g., solid cancer), desired therapeutic effects, administration method, treatment period, patient's age, patient's body weight, etc. For example, the content of the antibody in the pharmaceutical composition may be about 0.001 parts by weight to 10 parts by weight, based on 100 parts by weight of the entire pharmaceutical composition. The content of the cell in the pharmaceutical composition may be, for example, about 1 cell/mL to $10^4$ cells/mL.

The administration form of the pharmaceutical composition is not particularly limited as long as the desired effects are obtained. The pharmaceutical composition can be administered to mammals, including humans, by any of the following administration routes: oral administration and parenteral administration (e.g., intravenous injection, intramuscular injection, subcutaneous administration, rectal administration, dermal administration, and local administration). Since the active ingredient is a cell, the administration form is preferably parenteral administration, and more preferably intravenous injection. The dosage forms for oral administration and parenteral administration, and their production methods, are well known to a person skilled in the art. The pharmaceutical composition can be produced according to a usual method by, for example, mixing the antibody or cell of the present invention with a pharmaceutically acceptable carrier etc.

Examples of dosage forms for parenteral administration include injection preparations (e.g., intravenous drip infusion, intravenous injection, intramuscular injection, subcutaneous injection, and endodermic injection), external preparations (e.g., ointments, cataplasms, and lotions), suppositories, inhalants, eye drops, ophthalmic ointments, nasal drops, ear drops, liposome agents, and the like. For example, an injection preparation can be prepared by dissolving or suspending an antibody or cells in distilled water for injection, and optionally adding a solubilizer, a buffer, a pH adjuster, an isotonizing agent, a soothing agent, a preservative, a stabilizer, etc. The pharmaceutical composition can also be used as a freeze-dried preparation prepared before use.

The pharmaceutical composition may further comprise other drugs effective for the diagnosis, treatment, or prevention of diseases. The pharmaceutical composition can also contain components such as sterilants, antiphlogistics, cell activators, vitamins, and amino acids, if necessary.

As the carrier used for formulating the pharmaceutical composition, excipients, binders, disintegrators, lubricants, coloring agents, and flavoring agents that are generally used in this technical field can be used; and stabilizers, emulsifiers, absorption enhancers, surfactants, pH adjusters, antiseptics, antioxidants, extenders, moisturizers, surface activators, dispersants, buffers, preservatives, solubilizers, soothing agents, and the like can also optionally be used.

The type of disease diagnosed, treated, or prevented using the pharmaceutical composition is not particularly limited as long as the diagnosis, treatment, or prevention can be achieved. Examples of specific target diseases include cancer. The type of cancer is not particularly limited, and includes blood cancer and solid cancer. Examples of blood cancer include various B-cell malignant lymphomas (B-cell acute lymphocytic leukemia, follicular lymphoma, diffuse lymphoma, mantle cell lymphoma, MALT lymphoma, intravascular B-cell lymphoma, CD20-positive Hodgkin's lymphoma), myeloproliferative diseases, myelodysplastic/myeloproliferative tumors (CMML, JMML, CML, MDS/MPN-UC), myelodysplastic syndrome, acute myeloid leukemia, multiple myeloma, and the like. Examples of solid cancer include lung cancer, colorectal cancer, ovarian cancer, breast cancer, brain tumor, stomach cancer, liver cancer, tongue cancer, thyroid cancer, kidney cancer, prostate cancer, uterine cancer, osteosarcoma, chondrosarcoma, rhabdomyosarcoma, melanoma, neuroblastoma, bladder cancer, and the like.

The administration target (test subject) of the pharmaceutical composition is, for example, an animal having a disease described above or an animal with a potential to develop such a disease. A "potential to develop such a disease" can be determined by a known diagnostic method. The animal is, for example, a mammal, and preferably a human.

The dose of the pharmaceutical composition can be determined by a clinical physician, taking into consideration various factors, such as administration route, the type of disease, the degree of symptoms, patient's age, sex, and body weight, severity of disease, pharmacological findings, such as pharmacokinetics and toxicological characteristics, use or non-use of drug delivery system, and whether the composition is administered as part of a combinational drug with other medicinal agents. For example, when the active ingredient is the antibody, the dose of the pharmaceutical composition can be about 1 microgram/kg (body weight) to 10 g/kg (body weight) per day. When the active ingredient is the cell, the dose can be about $10^4$ cells/kg (body weight) to $10^9$ cells/kg (body weight). The administration schedule of the pharmaceutical composition can also be determined taking into consideration the same factors as those for the dose. For example, the composition can be administered once a day to once a month in the daily dose described above.

EXAMPLES

The present invention is described below in detail with reference to Examples; however, the present invention is not limited to these Examples.

Figure 1B:
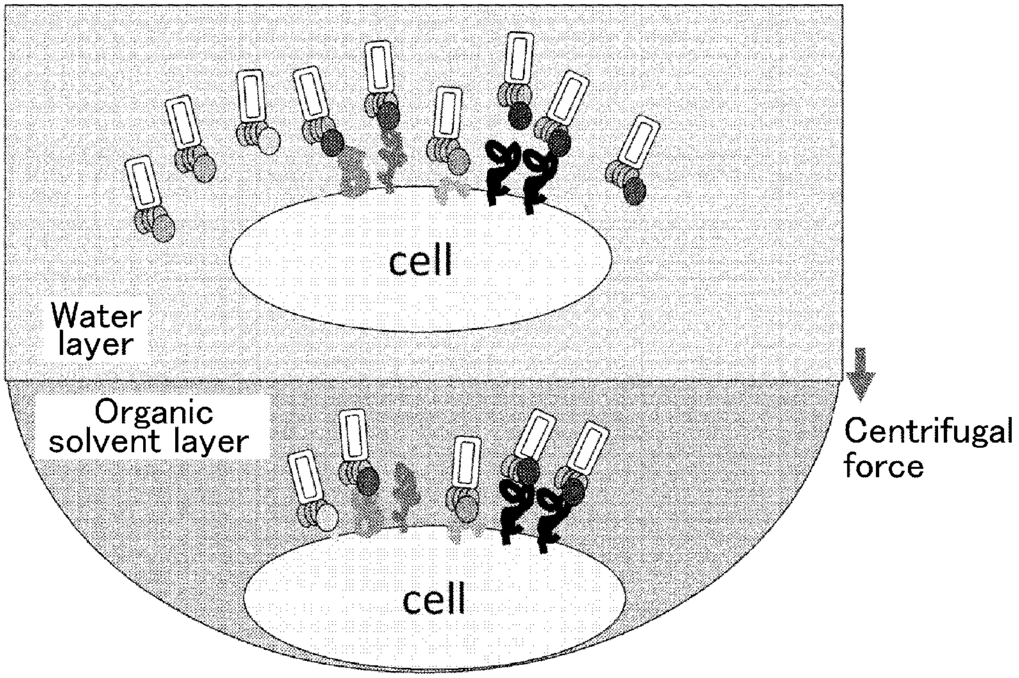
FIG. 1*b* is a schematic view of an antibody library screen method (cell screen) (Test Example 1). Polyclonal antibody clones obtained by the method of FIG. 1*a* were reacted with T2A24 cells peptide-pulsed with PRAME p301-309 and separated into a water layer and cell pellets using an organic solvent, and antibody clones bound to the cells were selected.

Test Example 1: Isolation and Evaluation of Antibody #98 that Recognizes HLA-A24-PRAME Using a human antibody library made in-house, an antibody library screen targeting an artificially prepared HLA-A24 PRAMEp301-309 (SEQ ID NO: 17) pMHC complex (hereafter referred to as "A24-PRAME") was performed, and multiple antibodies that recognize A24-PRAME were isolated. The method was performed according to the method described in NPL 7. Specifically, the antibodies were isolated using a phage display method. In this method, scFvCL is presented as part of phage coat protein cp3, and clones with high binding capability to the antigen can be selected by ELISA. After the magnet bead screen shown in FIG. 1*a* was performed twice, the cell screen shown in FIG. 1*b* was performed (NPL 8). About 400 clones were picked up, culture supernatants were prepared, and ELISA was performed for ScFvCL-CP3 obtained.

Figure 2:
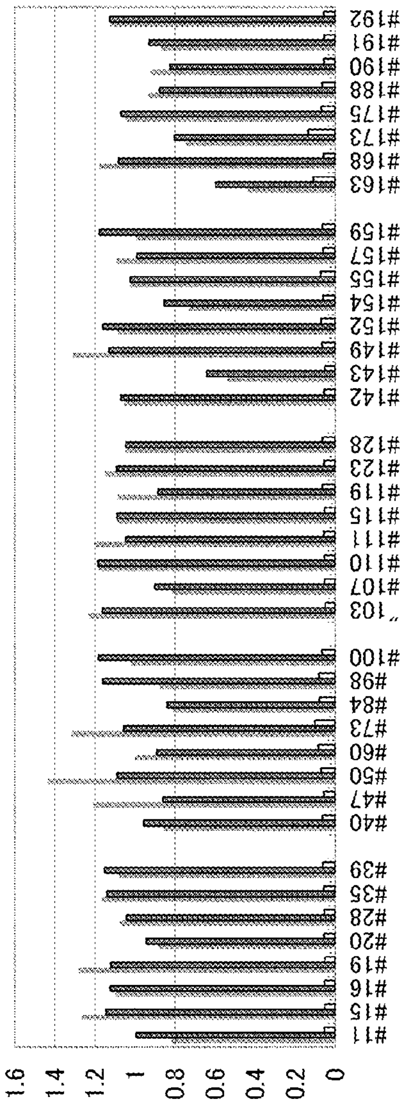
FIG. 2 shows the ELISA results for the antibodies of the clones obtained in Test Example 1. The vertical axis represents the relative value of the color development intensity, and the horizontal axis represents the clone number.

40 clones that reacted with A24-PRAME, which is a positive target, and did not react with A24-CMV, which is a negative target, were selected, and their recognition for two concentrations of A24-PRAME and one concentration of A24-CMV was examined by ELISA (FIG. 2). Specifically, *E. coli* culture supernatants of the 40 clones were prepared, and their recognition for A24-PRAME 100 ng/well (red), A24-PRAME 50 ng/well (black), and A24-CMV 100 ng/well (white) were examined by ELISA using 20 µl of each supernatant. After NeutrAvidin (Thermo) was immobilized on a MaxiSorp plate (NUNC), predetermined pMHC was reacted and immobilized, the culture supernatant of each clone was reacted with this, followed by washing and reacting with mouse anti-cp3 antibody (specially produced by MBL) and with HRP-labeled anti-mouse antibody (330, MBL), thereby making a determination by color development using TMB. Sequence analysis of these revealed that 13 kinds of antibodies were obtained.

Figure 3:
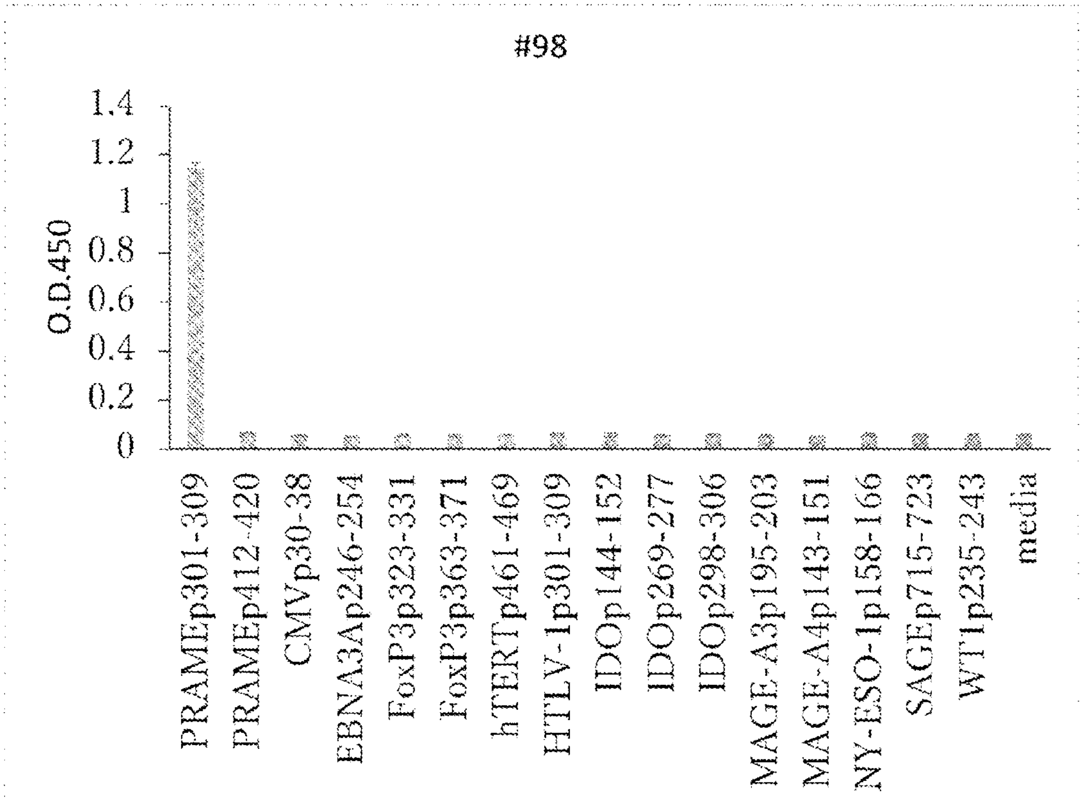
FIG. 3 shows the results of #98 scFvCL-cp3 by analyzing recognition for various HLA-A24-related pMHCs by ELISA (Test Example 1). It was confirmed that there was no reaction that is 1.5 times or more that of the background (none) in pMHC other than PRAME. The vertical axis represents the relative value of the color development intensity, and the horizontal axis represents the HLA-A24-related pMHCs used.

To examine the binding specificity of these antibodies, ELISA was performed using multiple peptide-HLA-A24 complexes (pMHCs). Each of the HLA-A24 pMHCs, i.e., A24-PRAME p301, PRAME p412, EBNA3A p246, MAGE-A3 p195, MAGE-A4 p143, SAGE p715, CMV p30, HTLV-1 p301, NY-ESO-1 p158, Foxp3 p323, Foxp3 p363, IDO p144, IDO p269, hTERT p461, and WT1 p235, was immobilized, and ELISA was performed using the selected antibodies. FIG. 3 shows the results of ELISA. The results showed that no cross recognition was observed for #98, indicating high specificity of recognition.

Figure 4:
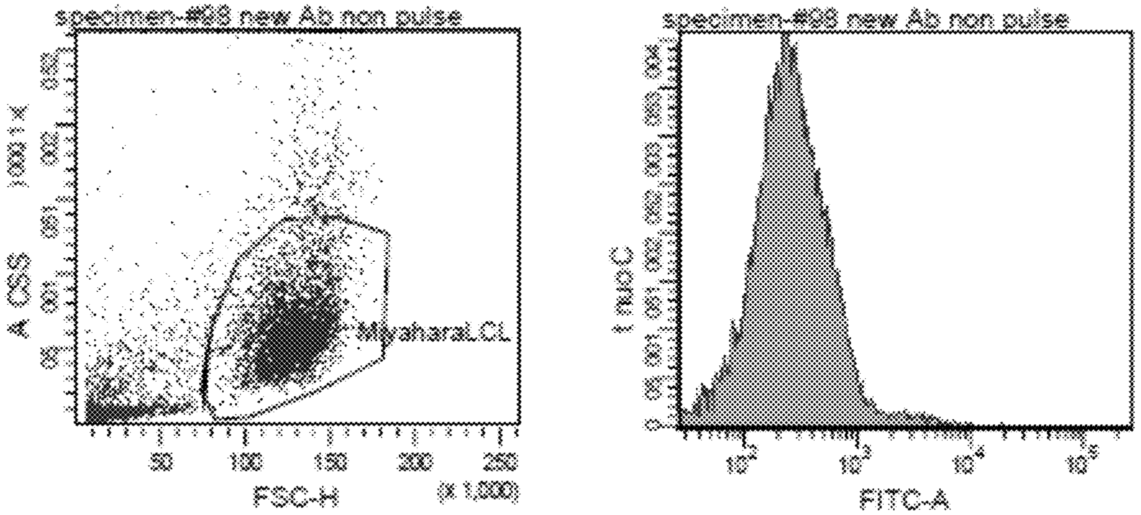
FIG. 4 shows the results of preparing A24-LCL cells without peptide pulsing and A24-LCL cells peptide-pulsed with PRAMEp301-309 at a concentration of 10 micromolar, reacting them with #98 scFvCL-cp3 antibody, then with anti-cp3 antibody (specially produced by MBL), and further with Alexa488-labeled anti-mouse IgG (Invitrogen), and performing measurement by Fluorescence-Activated Cell Sorting (FACS) using a FACSCANTO flow cytometer (Test Example 1).
Figure 4:
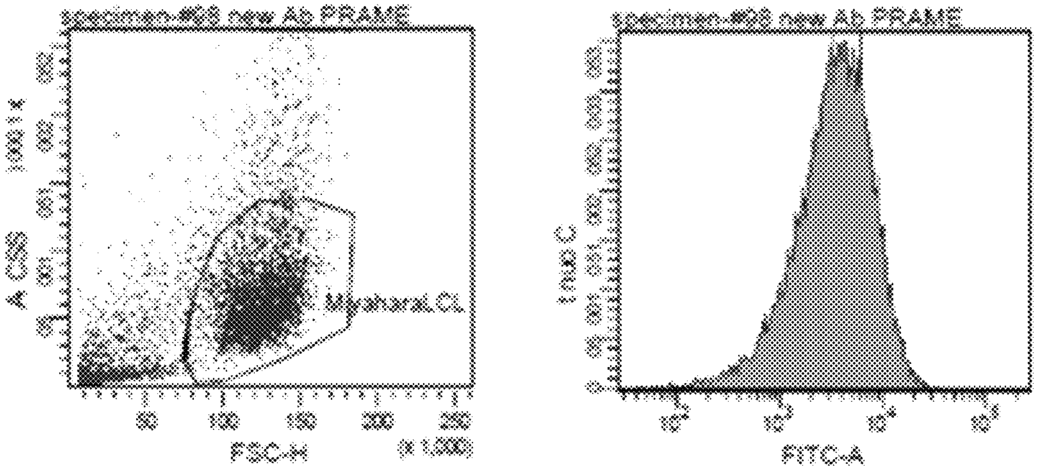

Next, the recognition for PRAMEp301-309 peptide-pulsed A24-LCL cells was examined in order to investigate whether a pMHC complex formed between cell-expressed HLA-A24 and PRAMEp301-309 was recognized. FIG. 4 shows the results. The results showed that sufficient recognition was observed in #98.

The amino acid sequence of antibody #98 and the base sequence encoding the antibody were analyzed. The analysis results are shown below. The sequences of the CDRs were deduced by IMGIT.

```
Heavy Chain
Heavy-chain CDR1 amino acid sequence:
                                        (SEQ ID NO: 1)
GGTFSSYA

Heavy-chain CDR2 amino acid sequence:
                                        (SEQ ID NO: 2)
IIPIFGTA

heavy-chain CDR3 amino acid sequence:
                                        (SEQ ID NO: 3)
ARHHSNYYYYGMDV

Heavy-chain variable region amino
acid sequence:
                                        (SEQ ID NO: 4)
QVQLVQSGAEVKKPGSSVKVSCKASGGTFSSYAIS

WVRQAPGQGLEWMGGIIPIFGTANYAQKFQGRVTI

TADESTGTAYMELSSLRSEDTAVYYCARHHSNYYY

YGMDVWGQGTTVTVSR

Heavy-chain CDR1 base sequence:
                                        (SEQ ID NO: 5)
GGAGGCACCTTCAGCAGCTATGCT

Heavy-chain CDR2 base sequence:
                                        (SEQ ID NO: 6)
ATCATCCCTATCTTTGGTACAGCA

Heavy-chain CDR3 base sequence:
                                        (SEQ ID NO: 7)
GCGAGACACCACAGTAACTACTACTACTACGGT
ATGGACGTC

Heavy-chain variable region base sequence:
                                        (SEQ ID NO: 8)
CAGGTGCAGCTGGTGCAGTCTGGGGCTGAGGTGAAGAAGC

CTGGGTCCTCGGTGAAGGTCTCCTGCAAGGCTTCTGGAGG

CACCTTCAGCAGCTATGCTATCAGCTGGGTGCGACAGGCC

CCTGGACAAGGGCTTGAGTGGATGGGAGGGATCATCCCTA

TCTTTGGTACAGCAAACTACGCACAGAAGTTCCAGGGCAG

AGTCACGATTACCGCGGACGAATCCACGGGCACAGCCTAC

ATGGAGCTGAGCAGCCTGAGATCTGAGGACACGGCCGTGT

ATTACTGTGCGAGACACCACAGTAACTACTACTACTACGG

TATGGACGTCTGGGGCCAAGGGACCACGGTCACCGTCTCG

AGA

Light Chain
Light-chain CDR1 amino acid sequence:
                                        (SEQ ID NO: 9)
NIGSKN

Light-chain CDR2 amino acid sequence:
                                       (SEQ ID NO: 10)
RDS

Light-chain CDR3 amino acid sequence:
                                       (SEQ ID NO: 11)
QVWDSSHV
```

-continued

Light-chain variable region amino acid sequence:

(SEQ ID NO: 12)

SYELTQPLSVSVALGQTARITCGGNNIGSKNVHWYQQKPG

QAPVLVIYRDSNRPSGIPERFSGSNSGNTATLTISRAQAG

DEADYYCQVWDSSHVFGTGTKVTVL

Light-chain CDR1 base sequence:

(SEQ ID NO: 13)

AACATTGGAAGTAAAAAT

Light-chain CDR2 base sequence:

(SEQ ID NO: 14)

AGGGATAGC

Light-chain CDR3 base sequence:

(SEQ ID NO: 15)

CAGGTGTGGGACAGCAGCCATGTC

Light-chain variable region base sequence:

(SEQ ID NO: 16)

TCCTATGAGCTGACTCAGCCACTCTCAGTGTCAGTGGCCC

TGGGACAGACGGCCAGGATTACCTGTGGCGGAAACAACAT

TGGAAGTAAAAATGTGCACTGGTACCAGCAGAAGCCAGGC

CAGGCCCCTGTGCTGGTCATCTATAGGGATAGCAACCGGC

CCTCTGGGATCCCTGAGCGATTCTCTGGCTCCAACTCGGG

GAACACGGCCACCCTGACCATCAGCAGAGCCCAAGCCGGG

GATGAGGCTGACTATTACTGTCAGGTGTGGGACAGCAGCC

ATGTCTTCGGAACTGGGACCAAGGTCACCGTCCTA

Test Example 2: Specific Recognition of A24-PRAME by #98 scFvCL-cp3

LCL cells have high expression of MHC-Class I. Thus, when LCL cells are pulsed with a peptide, the peptide is trapped on HLA-A24 on the LCL cells and presented as a pMHC. Thus, #98 was allowed to react with LCL cells pulsed with each of PRAME and CMV peptides and with DMSO, and sufficient recognition was confirmed by FACS.

Next, to investigate the amino acids involved in antibody recognition, peptides in which the amino acids of PRAME p301-309 (LYVDSLFFL, Table 1, SEQ ID NO: 17) were replaced one by one with other amino acids (mainly alanine) were prepared (Table 1, SEQ ID NOs: 18-26). Since 2Y and 9L were predicted to be anchor amino acids, 2F, 2W, 9F, and 9I (Table 1, SEQ ID NOs: 27-30), which stabilize peptide binding, were also examined, and antibody recognition changes due to peptide changes were examined. Specifically, wild type, DMSO, and peptides containing 1A, 2A, 3A, 4A, 5A, 6A, 7A, 8A, 9A, 2F, 2W, 9F, and 9I were prepared, A24-LCL was peptide-pulsed with each of them at a concentration of 10 micromolar, reacted with #98 scFvCL-cp3, then reacted with mouse-anti-cp3 antibody, and then reacted with Alexa488-labeled anti-mouse antibody, and measurement was performed using a FACSCANTO flow cytometer.

TABLE 1

| pep No | name | sequence (SEQ ID NO) |
|---|---|---|
| 1 | p301-309 | LYVDSLFFL (17) |
| 2 | p301-1A | AYVDSLFFL (18) |
| 3 | p301-2A | LAVDSLFFL (19) |
| 4 | p301-3A | LYADSLFFL (20) |
| 5 | p301-4A | LYVASLFFL (21) |
| 6 | p301-5A | LYVDALFFL (22) |
| 7 | p301-6A | LYVDSAFFL (23) |
| 8 | p301-7A | LYVDSLAFL (24) |
| 9 | p301-8A | LYVDSLFAL (25) |
| 10 | p301-9A | LYVDSLFFA (26) |
| 11 | p301-2W | LWVDSLFFL (27) |
| 12 | p301-2F | LFVDSLFFL (28) |
| 13 | p301-9F | LYVDSLFFF (29) |
| 14 | p301-9I | LYVDSLFFI (30) |

Figure 5:
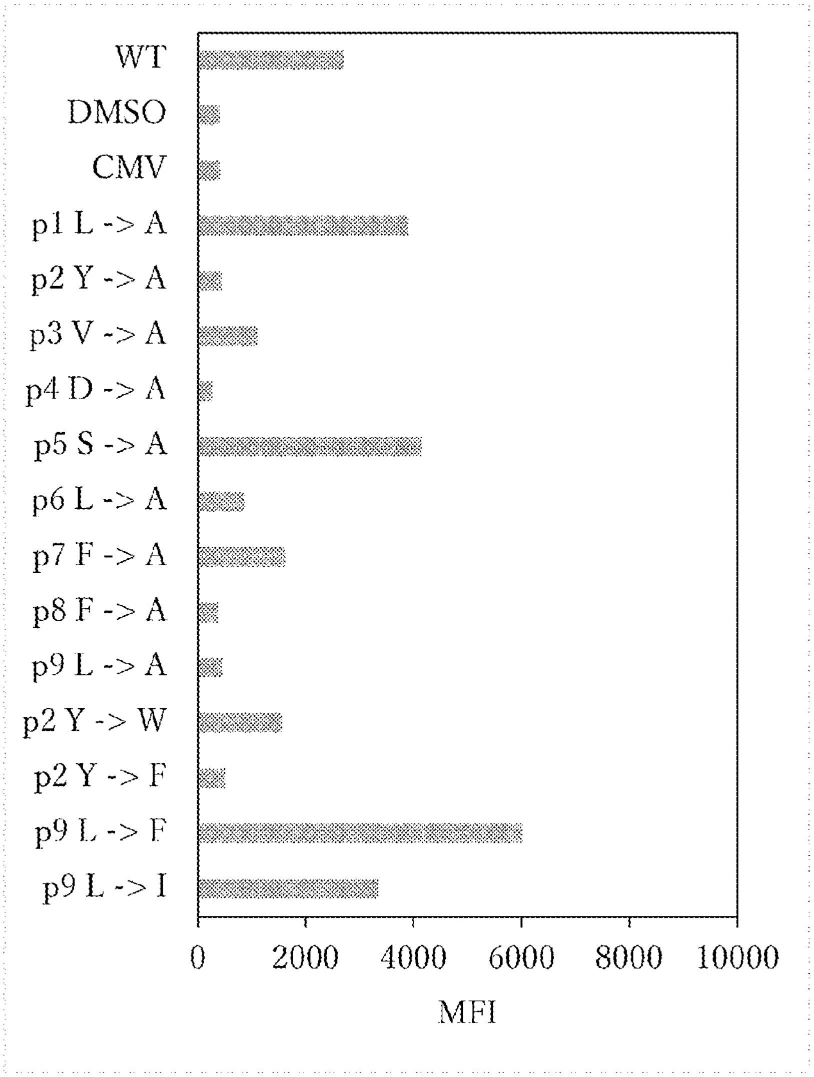
FIG. 5 shows the results of alanine substitution investigation (Test Example 2). The vertical axis represents the substitution site and the amino acid after substitution in the peptides used, and the horizontal axis represents the average fluorescence intensity.

As a result, as shown in FIG. 5, in #98, the MFI values were decreased in the cases of 2A, 3A, 4A, 6A, 7A, 8A, and 9A, indicating that these seven amino acids are essential for antibody recognition. The MFI did not decrease in the case of 9F or 9I, indicating that these amino acids can be recognized (FIG. 5). Thus, xYVDxLFFL (SEQ ID NO: 31), xYVDxLFFF (SEQ ID NO: 32), and XYVDxLFFI (SEQ ID NO: 33) were considered as motifs for risk search.

Test Example 3: Measurement of Association Constant of #98 SCFvCL-pp

Figure 6:
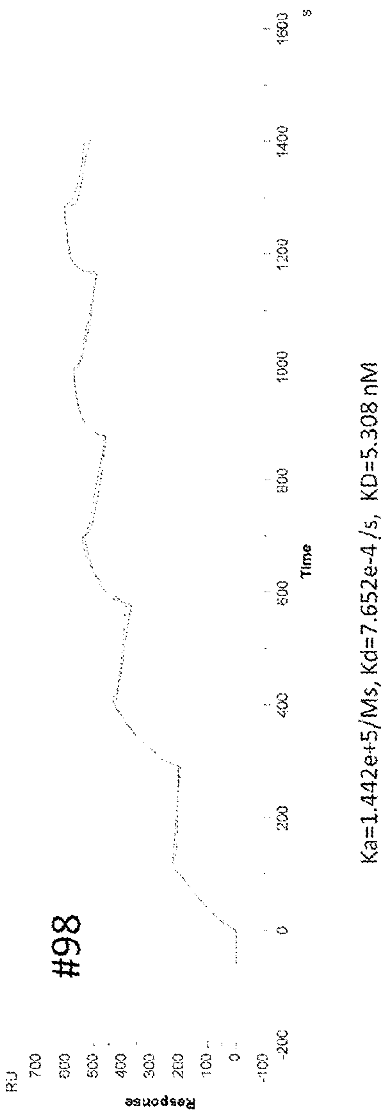
FIG. 6 shows the affinity measurement results by the Surface Plasmon Resonance (SPR) method for #98 (Test Example 3).

Next, the KD value of #98 scFvCL-cp3 pp, which was generated by converting #98 scFvCL-cp3 to pp form, was measured using a BIACORE X100 SPR system. The KD value was determined with SPR by measuring dynamic changes in detection sensitivity (resonance, reflecting the change in mass on the chip) over time. The dissociation rate constant (Kd) and association rate constant (Ka) were determined from the dynamic change curve, and the association constant was determined from the ratio of the two constants. Specifically, each scFv-cp3 expression plasmid was cleaved with restriction enzyme SalI, subjected to self-ligation, and used to transform *E. coli* DH5a, thereby obtaining a clone that produces scFv-pp. The clone was cultured in medium containing IPTG, the supernatant was collected, concentrated with ammonium sulfate, purified with IgG Sepharose 6 Fast Flow, and dialyzed with PBS, and the concentration was estimated by SDS-PAGE. SPR measurement using a BIACORE X100 SPR system was performed using Biotin CAPture Kit (GE) according to the manufacturer's instructions. Specifically, first, A24 PRAMEp301-309 was immobilized on the sensor chip as a ligand. Next, five concentrations, i.e., 500 nM, 250 nM, 125 nM, 62.5 nM, and 31.25 nM, of scFv-pp were sequentially reacted, and association and dissociation were measured. Global fit was performed on this, and Kon, Koff, and KD were calculated. The measurement results revealed that the association constant of #98 scFvCL-pp was 5.3 nM (FIG. 6).

Figure 7:
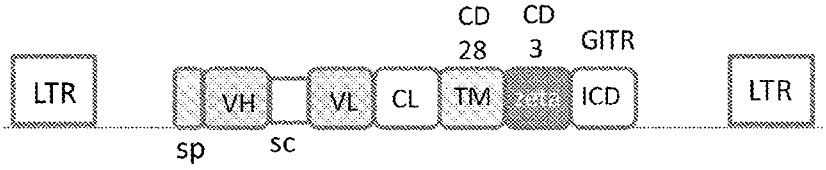
FIG. 7 is a schematic view of a retroviral vector for CAR introduction (Test Example 4).
Figure 8A:
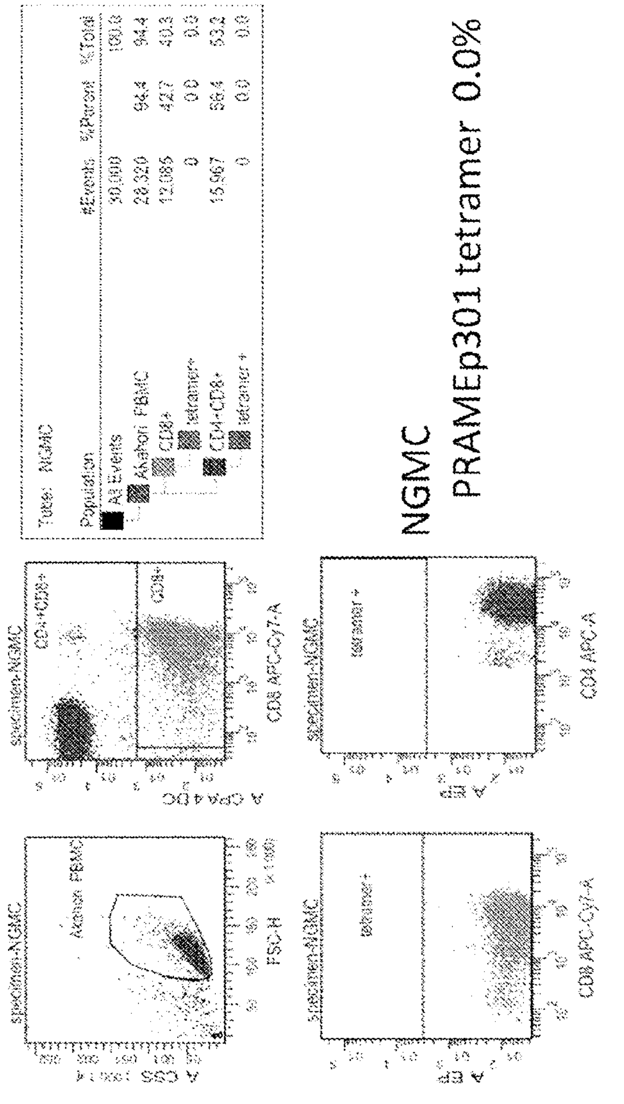
FIG. 8*a* shows the FACS results of CAR-untransduced cells (Test Example 4).
Figure 8B:
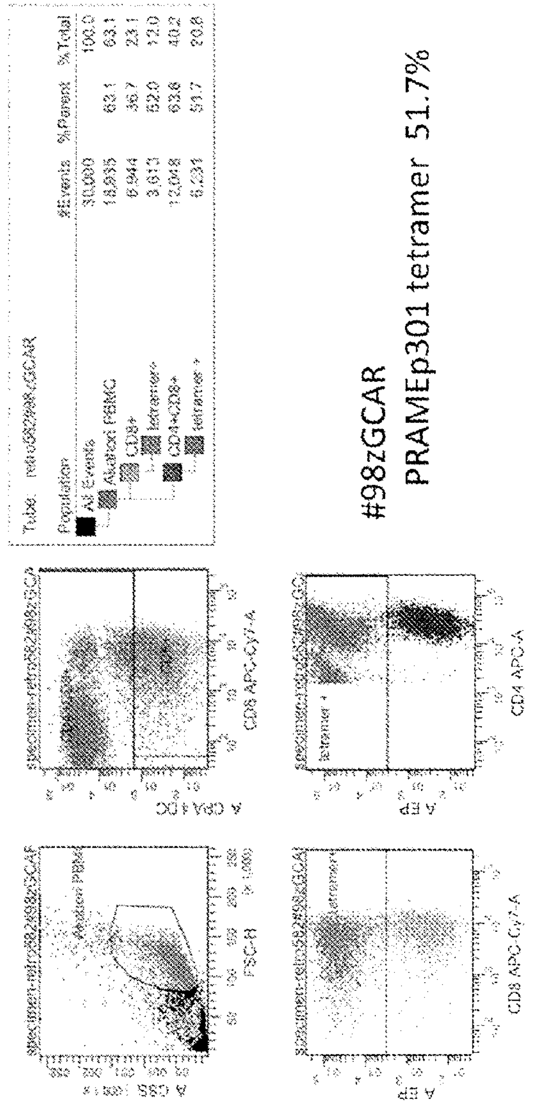
FIG. 8*b* shows the FACS results of CAR-transduced cells (Test Example 4).

Test Example 4: Production of Retroviral Vector, Introduction into PBMC, and Investigation of Expression Retroviral gene transfer was performed for constitutive CAR expression. CAR-T cells were produced by constructing a retroviral vector for CAR introduction (FIG. 7), producing retroviruses using packaging cells Plat-A, and infecting PBMCs with the retroviruses. CAR expression was checked by tetramer staining. Specifically, human PBMCs were stimulated with OKT3 and RetroNectin, cultured, infected with the produced retroviruses on day 3 and day 4, and cultured to produce CAR-T cells (FIG. 8). These cells were stained with PRAME tetramer and anti-CD4 and anti-CD8 antibodies, and measurement was performed using a FACSCANTO flow cytometer. The results revealed that the CAR positive percentage of CAR-T cells was 52.0% for CD8 and 51.7% for CD4 (FIG. 8).

Figure 9:
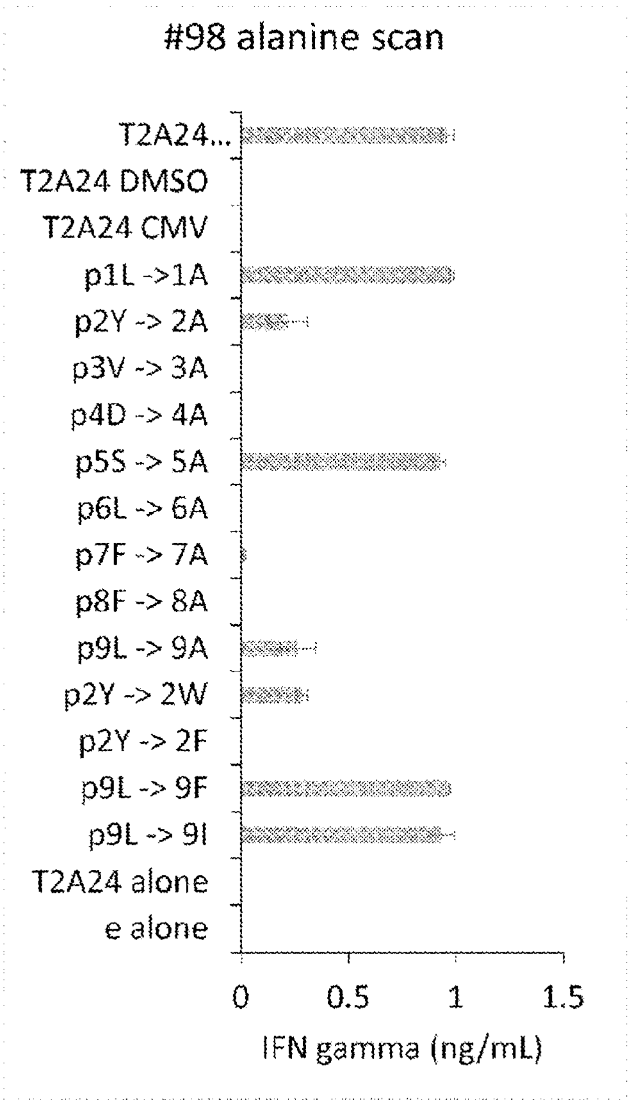
FIG. 9 shows the results of alanine substitution investigation on CAR-transduced cells (Test Example 5). The vertical axis represents the substitution site and the amino acid after substitution in the peptides used, and the horizontal axis represents the IFN gamma concentration.

Test Example 5: Investigation of Alanine Scan of #98 zG CAR-T Cells and Risk Assessment T2A24 cells pulsed with each of the alanine scan peptides described in Test Example 2 were co-cultured with #98 zG CAR-T cells, and the amounts of IFNg secreted into the culture supernatants were measured by ELISA (FIG. 9). Specifically, $1\times10^5$ A24-LCL cells pulsed with each of the amino acid substituted peptides shown in FIG. 5 were co-cultured with the same number of #98 CAR-T cells, and the amounts of IFNg produced for 24 hours were detected by ELISA and compared. The pattern was similar to that in the alanine scan using scFvCL-cp3, with clear recognition for 1A, 5A, 9F, and 9I. Thus, BLAST searches were performed using XYVDxLFFL (SEQ ID NO: 31), XYVDXLFFF (SEQ ID NO: 32), and xYVDxLFFI (SEQ ID NO: 33) as motifs. As a result, no peptides matching these motifs were extracted.

Figure 16:
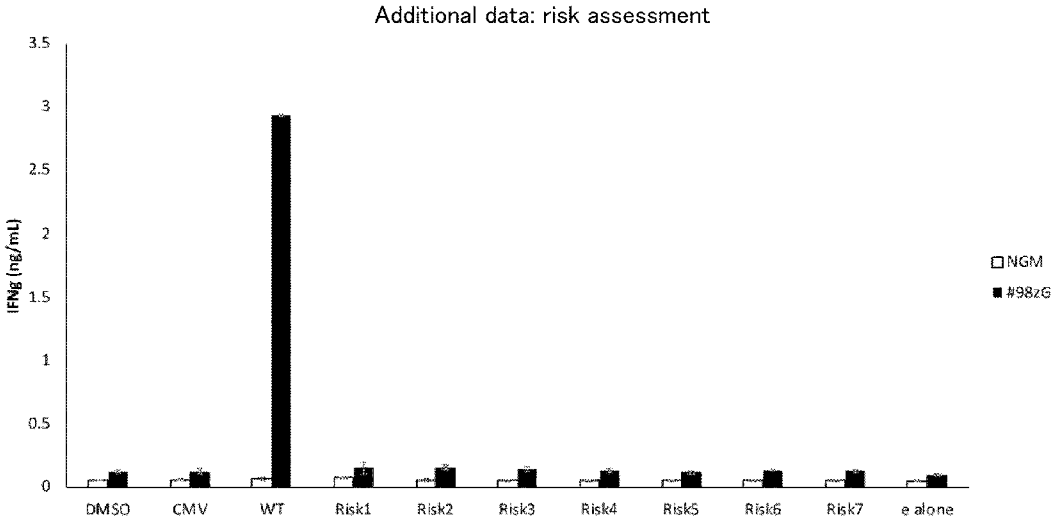
FIG. 16 shows the results of pulsing T2A24 with the peptides in Table 2, CMV, and DMSO, co-culturing the cells with #98 CAR-T cells, and measuring the amount of IFNg secreted in the culture supernatants by ELISA (Test Example 5). The vertical axis represents the amount of IFNg, and the horizontal axis represents the peptides used. Note that "e alone" indicates only effector cells.

Further, Table 2 shows genes encoding amino acid sequences that differ from the amino acid sequence of PRAMEp301-309 by three amino acids in the BLAST searches. T2A24 was pulsed with these peptides, CMV, and DMSO, and co-cultured with #98 CAR-T cells. The amounts of IFNg secreted in the culture supernatants were measured by ELISA. Note that “e alone” indicates only effector cells (FIG. 16). No response of #98 CAR-T cells to the peptides listed in Table 2 was observed.

TABLE 2

| | gene name | sequence |
|---|---|---|
| | PRAME | LYVDSLFFL (SEQ ID NO: 17) |
| risk 1 | F-box only protein 24 isoform 3 | DYVGTLFFL (SEQ ID NO: 34) |
| risk 2 | pre-mRNA-processing factor 40 homolog A isoform X5 | IYEDVLFFL (SEQ ID NO: 35) |
| risk 3 | Pre-mRNA-processing factor 40 homolog B | VYDDVLFFL (SEQ ID NO: 36) |
| risk 4 | cytoskelton associated protein 5 | LYVDLLFFP (SEQ ID NO: 37) |
| risk 5 | potassium channel subfamily K member 12 | DYVDSLYFC (SEQ ID NO: 38) |
| risk 6 | DENN domain-containing protein 4B isoform 2 | RDVDNLFFL (SEQ ID NO: 39) |
| risk 7 | CSGlcA-T protein | HPVDTLFFL (SEQ ID NO: 40) |

Test Example 6: Recognition Avidity Evaluation of #98 zG CAR

Figure 10:
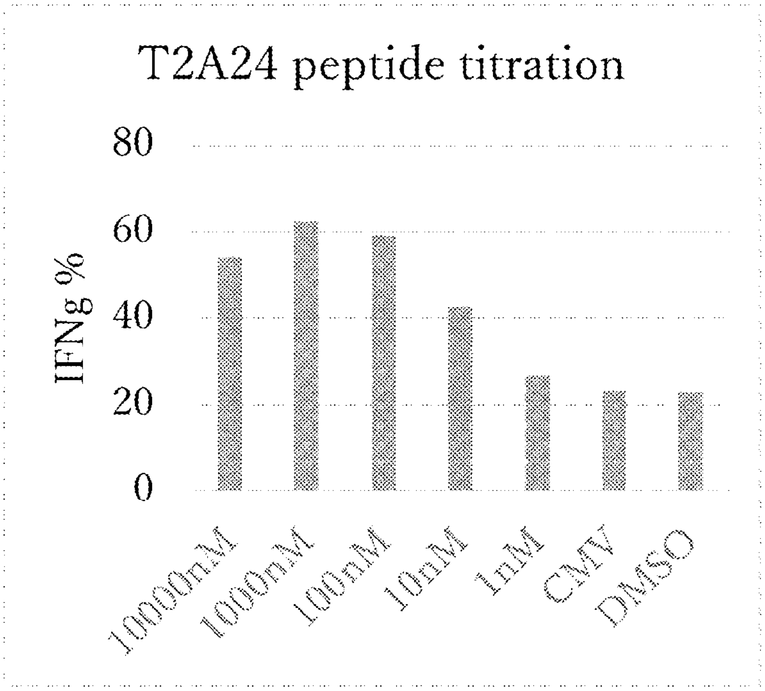
FIG. 10 shows the FACS results of CAR-transduced cells stained for IFNg (Test Example 5). The vertical axis represents the IFNg positive percentage, and the horizontal axis represents the PRAME p301-309 concentration in peptide pulsing.

T2A24 cells were pulsed with different concentrations Of PRAME peptide and co-cultured with #98 zG CAR-T cells, intracellular staining of IFNg was performed, and the recognition by #98 zG CAR-T cells was measured. This is avidity. Specifically, T2A24 cells were peptide-pulsed with PRAME p301-309 at concentrations of 10, 1, 0.1, 0.01, and 0.001 micromolar, CMV at a concentration of 10 micromolar, and DMSD, reacted and co-cultured for 6 hours with #98 CAR-T cells, PEcy7-labeled CD8+ RPE-labeled tetramer+ CAR-T cells were stained with APC-labeled anti-IFNg antibody, and the reacted CAR-T cells were measured using a FACSCANTO flow cytometer. The IC50 was about 10 nM, and it was found that there was sufficient recognition activity (FIG. 10).

Test Example 7: Specific Recognition of A24+PRAME+ Target Cells by #98 zG CAR-T Cells PRAME expression in the target cells used in this test was analyzed. Specifically, total RNA was extracted from cultured cells using an RNA extraction kit (Promega), followed by reverse transcription reaction. PRAME (Hs01022301_ml) and GAPDH CONTROL MIX (REF 4325792), which are TaqMan gene expression assay reagents sold by Applied Biosystems, were used for RT-PCR. The expression level of PRAME was normalized by the expression level of GAPDH.

Further, the HLA-A24 expression in the target cells used in this test was analyzed. Specifically, T2A24, SK-MEL-124, and NW-MEL-38 were stained with Bulk Monoclonal Antibody A23, 24 IgG2b (One Lambda, Inc.) as a primary antibody and Alexa Fluor 488 goat anti-mouse IgG (H+L) (Invitrogen) as a secondary antibody. Measurement was performed by flow cytometry.

Figure 11A:
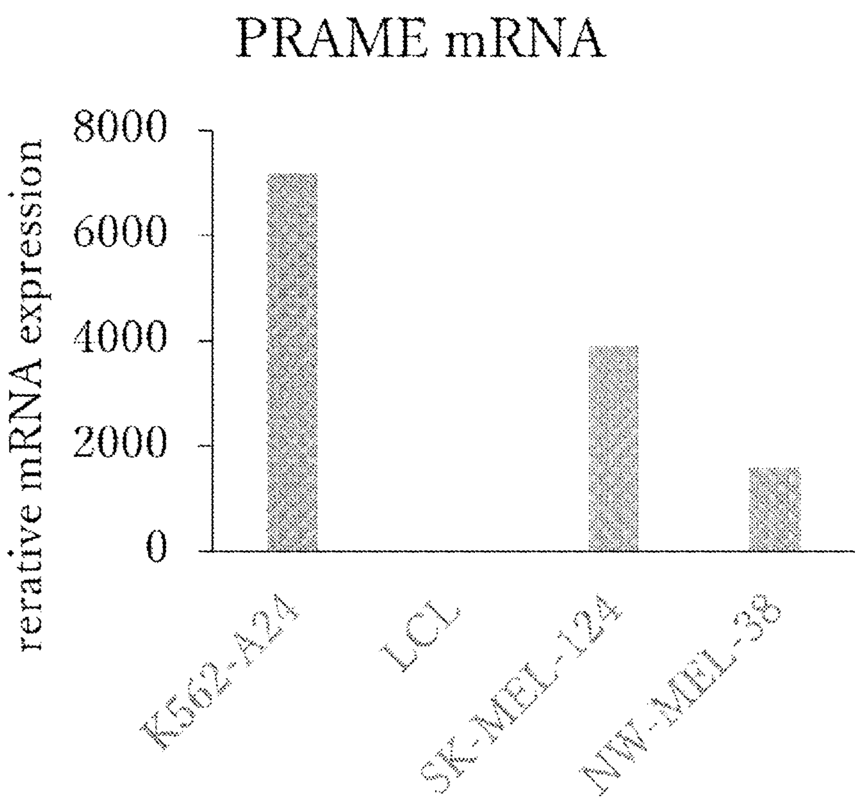
FIG. 11*a* shows the results of PRAME expression analysis of target cells in Test Examples 7 and 8. The vertical axis represents the relative value of the PREME mRNA level, and the horizontal axis represents the target cells.
Figure 11B:
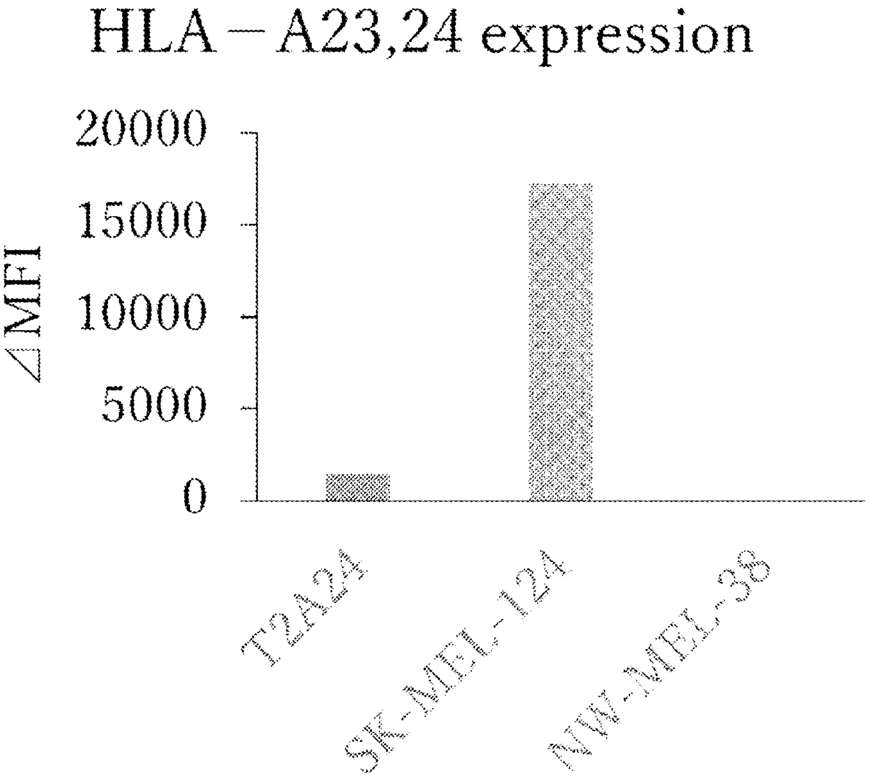
FIG. 11*b* shows the results of HLA-A24 expression analysis of target cells in Test Examples 7 and 8. The vertical axis represents the average fluorescence intensity for HLA-A24, and the horizontal axis represents the target cells.

FIG. 11*a* and FIG. 11*b* show the results. A24-transduced NW-MEL-38 and SK-MEL-124 express HLA-A24 and PRAME and are thus positive targets. On the other hand, NW-MEL-38 is a negative target because it does not express HLA-A24. T2A24 cells do not express PRAME.

Figure 12:
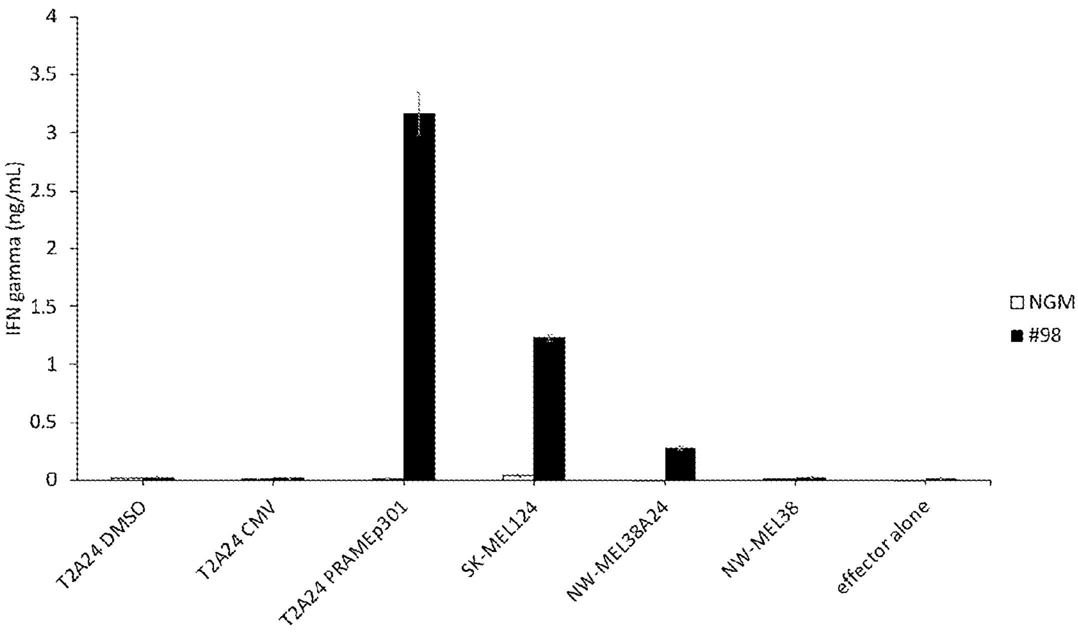
FIG. 12 shows the measurement results of the IFN gamma concentration by ELISA in Test Examples 7 and 8. The vertical axis represents the IFN gamma concentration, and the horizontal axis represents the target cells.

Retrovirally transduced CAR-T cells were co-cultured with peptide-pulsed target cells for 24 hours, and IFN-γ in the culture supernatants was measured. IFN-γ production was increased specifically in PRAME-pulsed LCL cells. In co-culture with CMV-pulsed T2A24 cells, a negative control, no IFN-γ production was observed (FIG. 12). In addition, tumor-specific IFN-γ production was observed in A24-positive PRAME-positive SK-MEL-124 and A24 gene-transduced NW-MEL-38, both of which are target cells, and a clear difference from off-target NW-MEL-38 was observed (FIG. 12). Thus, it was confirmed that by introducing the CAR gene by a retroviral vector, the CAR is expressed, specifically recognizes a tumor, and produces IFN-γ.

Test Example 8: Specific Recognition of Target Cancer Cells by CAR-T Cells into Which PRAME #98 CAR Gene Is Introduced IFNg production was observed in co-culture of #98 CAR-T cells with PRAMEp301-309 peptide-pulsed T2A24 cells, indicating that the #98 CAR-T cells recognized the positive target. In contrast, IFNg production was not observed in co-culture with CMV peptide-pulsed T2A24 cells and T2A24 cells without peptide pulsing, indicating that the #98 CAR-T cells did not recognize these negative targets (FIG. 12).

Next, recognition for cultured cancer cells was examined. PRAME expression in the cultured cells used is shown in FIG. 11*a*, and HLA-A24 expression is shown in FIG. 11*b*. NW-MEL-38-HLA-A24 (NW-MEL-38 cells were retrovirally transduced with the HLA-A24 gene to forcibly express HLA-A24; PRAME-positive HLA-A24-positive) and SK-MEL-124 (PRAME-positive HLA-A24-positive) were positive target cells, whereas NW-MEL-38 (PRAME-positive HLA-A24-negative) is a negative target cell. As shown in FIG. 12, IFNg production was observed in co-culture of #98 CAR-T cells with the positive cells, and no IFNg production was observed in co-culture of #98 CAR-T cells with the negative cells, thus indicating that the #98 CAR-T cells specifically recognized the target cells.

Test Example 9: Specific Recognition of Target Cancer Cells by CAR-T Cells into Which PRAME #98 CAR Gene Is Introduced NW-MEL-38-HLA-A24 (NW-MEL-38 cells were retrovirally transduced with the HLA-A24 gene to forcibly express HLA-A24; PRAME-positive HLA-A24-positive) and SK-MEL-124 (PRAME-positive HLA-A24-positive) as positive target cells, and NW-MEL-38 (PRAME-positive HLA-A24-negative) as negative target cells were seeded on E-plates. After 24.5 hours, #98 CAR-T cells were allowed to act as effector cells, and index changes were observed using RTCA. The details are as follows.

Figure 13A:
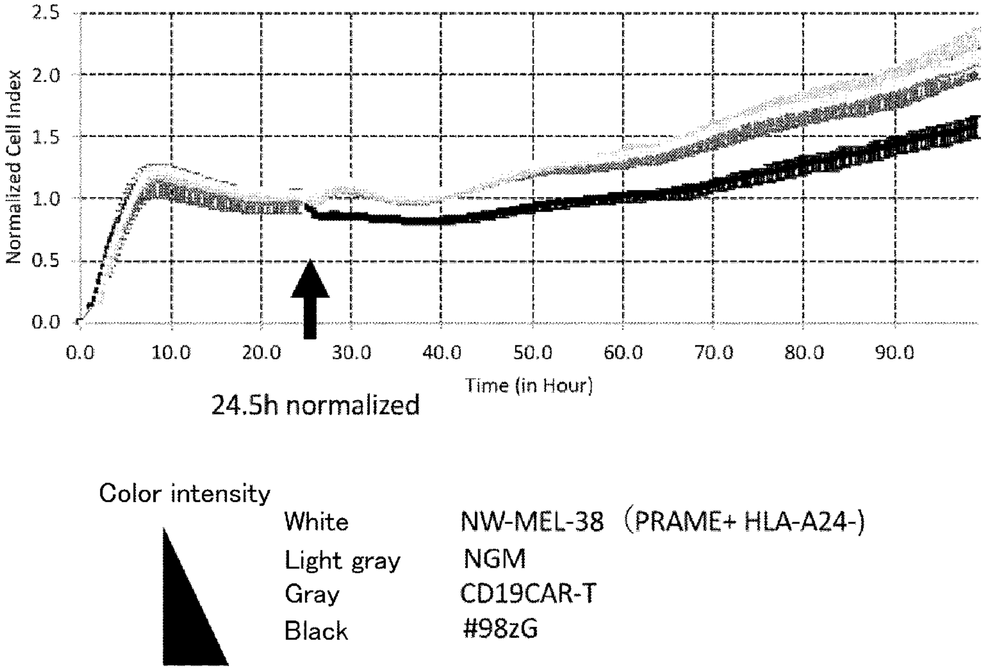
FIG. 13*a* shows the results of observing changes in the index using an XCELLIGENCE Real-Time Cell Analysis (RTCA) system by allowing each kind of effector cells to act on negative target cells (NW-MEL-38 (PRAME-positive HLA-A24-negative)). The vertical axis represents the number of A24 NW-MEL-38 cells normalized on the assumption that the number of NW-MEL-38 cells immediately before co-culture with the effector cells was 1. The horizontal axis represents the elapsed time from the start of culture. The legend shows the effector cells.

After 7000 negative target cells NW-MEL-38 (A24-PRAME+) were cultured on an E-plate for 24.5 hours, each kind of effector cells (100000 cells) was added and cultured, and the cell index was monitored over time. The cell index reflects the number of A24 NW-MEL-38 cells on the E-plate. The normalized cell index is a cell index normalized on the assumption that the number of NW-MEL-38 cells immediately before co-culture with the effector cells was 1. FIG. 13*a* shows the results. The graph shows the average values (n=3). Cytotoxicity by the #98 CAR-T cells was minor.

Figure 13B:
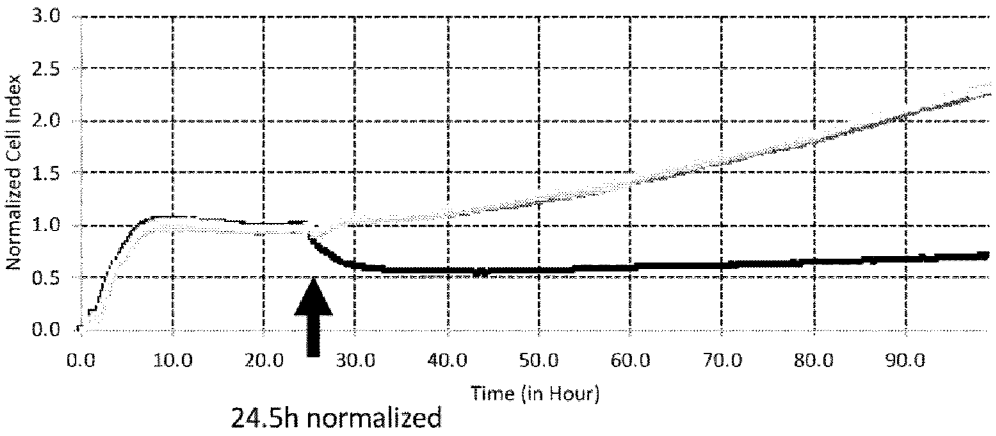
FIG. 13*b* shows the results of observing changes in the index by RTCA by allowing each kind of effector cells to act on positive target cells (HLA-A24-transduced NW-MEL-38 cells (A24+PRAME+)). The vertical axis represents the number of A24 NW-MEL-38 cells normalized on the assumption that the number of NW-MEL-38 cells immediately before co-culture with the effector cells was 1. The horizontal axis represents the elapsed time from the start of culture. The legend shows the effector cells.

After 7000 HLA-A24-transduced NW-MEL-38 cells (A24+PRAME+) were cultured on an E-plate for 24.5 hours, each kind of effector cells (100000 cells) was added and cultured, and the cell index was monitored over time. The cell index reflects the number of A24 NW-MEL-38 cells on the E-plate. The normalized cell index is a cell index normalized on the assumption that the number of A24 NW-MEL-38 cells immediately before co-culture with the effector cells was 1. FIG. 13*b* shows the results. The graph shows the average values (n=3). Cytotoxicity by the #98 zG CAR-T cells was observed, and no cytotoxicity by the CD19 zG CAR-T cells or the PBMCs into which CAR was not introduced was observed.

Figure 13C:
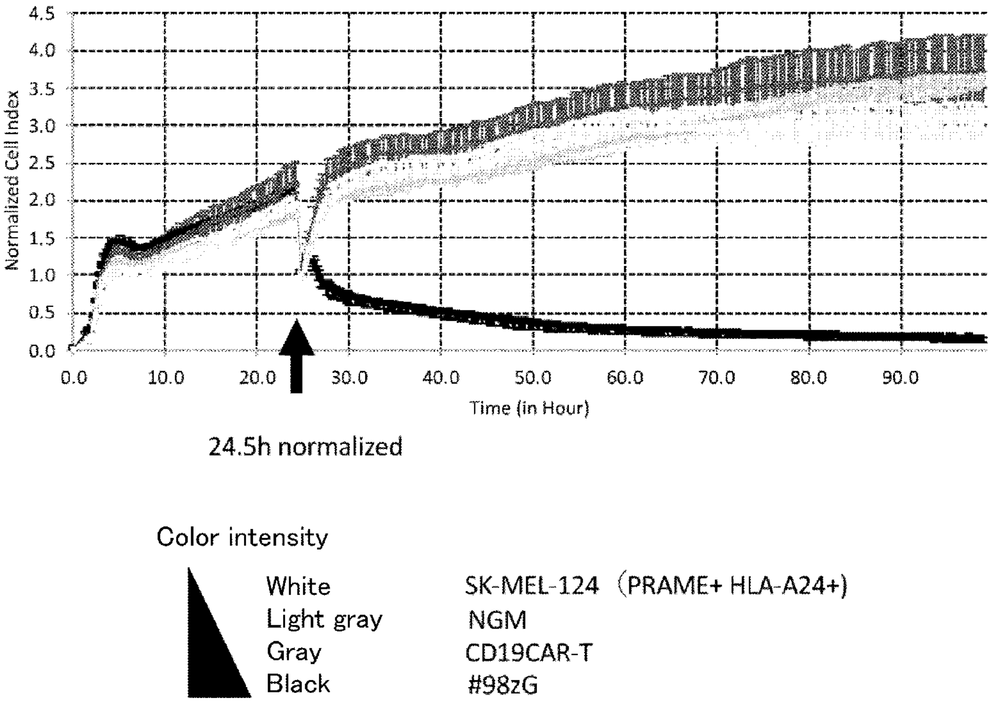
FIG. 13*c* shows the results of observing changes in the index by RTCA by allowing each kind of effector cells to act on positive target cells (SK-MEL-124 cells (A24+PRAME+)). The vertical axis represents the number of A24 NW-MEL-38 cells normalized on the assumption that the number of NW-MEL-38 cells immediately before co-culture with the effector cells was 1. The horizontal axis represents the elapsed time from the start of culture. The legend shows the effector cells.

After 7000 SK-MEL-124 cells (A24+PRAME+) were cultured on an E-plate for 24.5 hours, each kind of effector cells (100000 cells) was added and cultured, and the cell index was monitored over time. The cell index reflects the number of SK-MEL-124 cells on the E-plate. The normalized cell index is a cell index normalized on the assumption that the number of A24 NW-MEL-38 cells immediately before co-culture with the effector cells was 1. FIG. 13*c* shows the results. The graph shows the average values (n=3). Cytotoxicity by the #98 zG CAR-T cells was observed, and no cytotoxicity by CD19 zG or PBMCs into which CAR was not introduced was observed.

As shown in FIGS. 13*a*, 13*b*, and 13*c*, a cytotoxic effect on NW-MEL-38-HLA-A24 and SK-MEL-124, which are A24+PRAME+, was observed, and a cytotoxic effect on NW-MEL-38, which is A24-, was not observed, indicating that cytotoxicity of the #98 CAR-T cells is positive target cell-specific.

Test Example 10: Cancer Suppression 1 by #98 zG CAR-T Cells

Figure 14A:
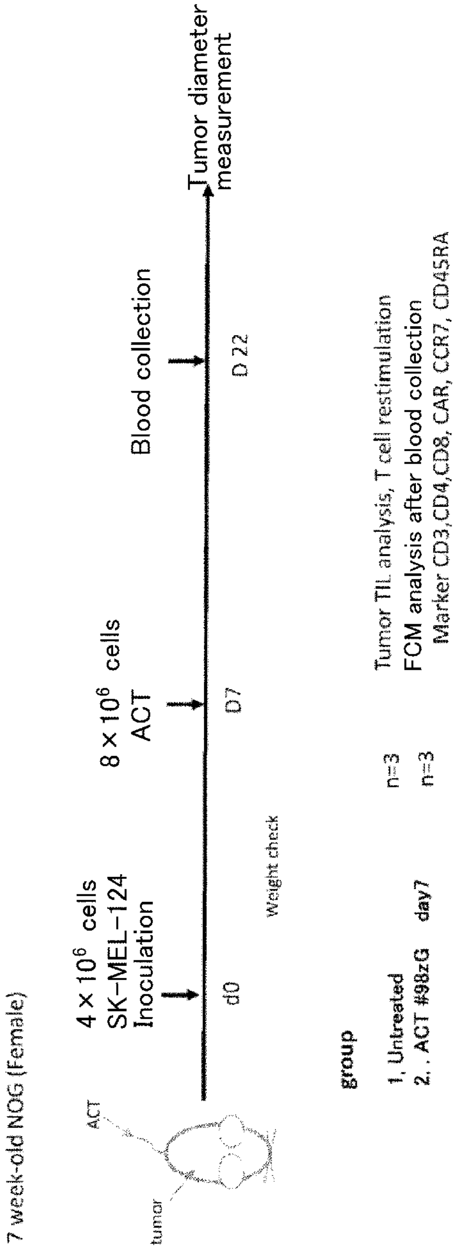
FIG. 14*a* shows the outline of the test of Test Example 10.

Since NOG mice lack a common γ receptor, there are no NK cells in the mice. Thus, NOG mice show notably better engraftment of human cells and human tissues than NOD-SCID mice, and human cancer and human normal tissues can be engrafted in NOG mice at high rates. In addition, human T-cell differentiation is observed after transplantation of human hematopoietic stem cells; thus, demand for NOG mice as human immune system model mice is increasing. The characteristics of NOG mice include deletion of T cells and B cells, deletion of natural killer (NK) cells, reduced dendritic cell function, reduced macrophage function, loss of complement activity, and no leakiness of T cells and B cells associated with aging. NW-MEL-124 (A24-positive PRAME-positive) cells were transplanted into the right flank of NOG mice at $4\times10^6$ cells/mouse. On day 7, PRAME #98 CAR-T cells sorted with anti-lambda antibody were infused into the mice via a tail vein at $8\times10^6$ cells/mouse. The details are as follows (the outline is shown in FIG. 14*a*). 7-week-old female NOG mice were purchased and acclimated for 1 week, and $4\times10^6$ SK-MEL-124 cells were transplanted into the mice by subcutaneous injection. Effector cells were reacted with RPE-labeled anti-rabbit antibody after reaction with anti-lambda antibody and sorted with anti-PE beads to purify the cells. The purified effector cells were infused into the mice by intravenous administration on day 7 after target cell inoculation. In the control, nothing was infused.

Gene transfer to CAR-T cells was performed according to the method of Test Example 8. CD8 and CD4 were present at 95.2% and 2.1%, and the CAR positive percentage was 97% for CD8 and 98.8% for CD4.

An experiment was performed in the CAR-T cell infusion group (n=3) and untreated group (n=3), and the tumor diameter was measured every 3 to 4 days. Measurement was performed until day 50 after tumor transplantation.

Figure 14B:
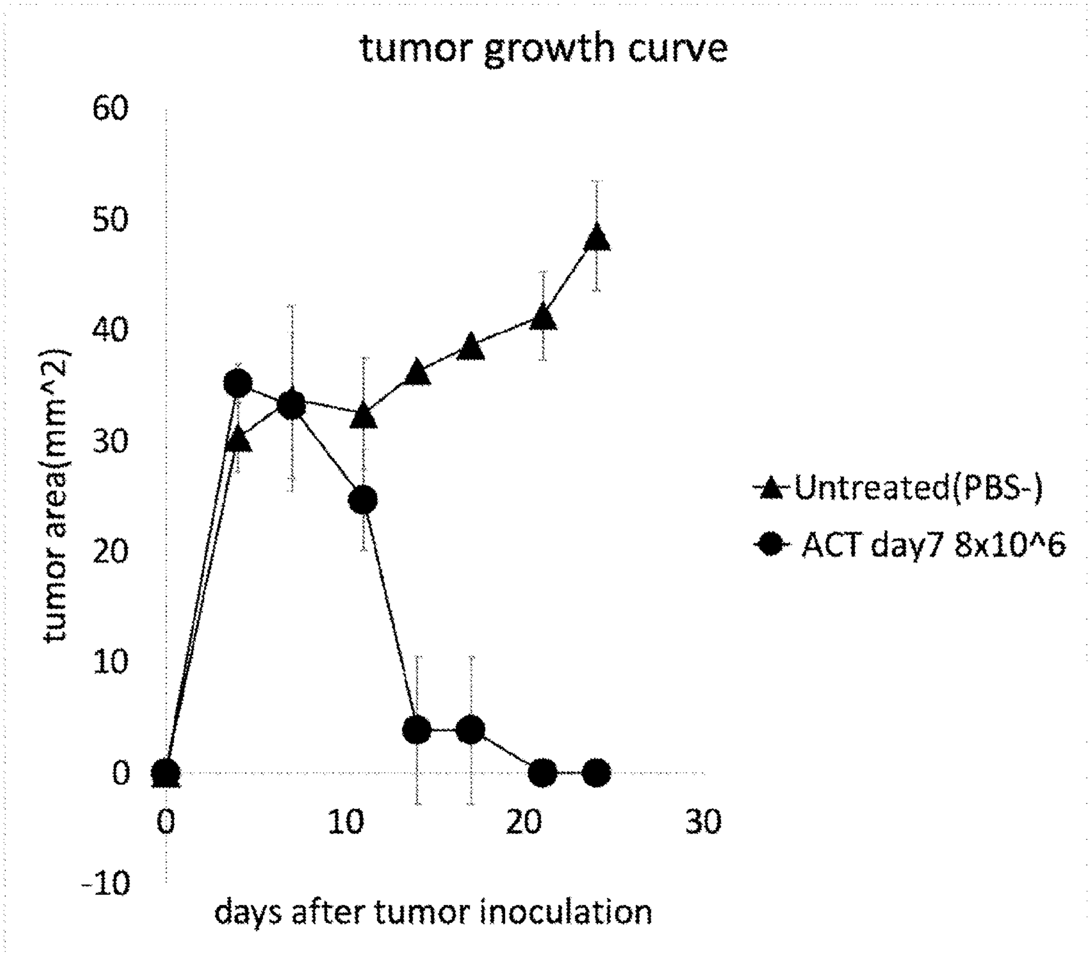
FIG. 14*b* shows the measurement results of the area of the tumor region in Test Example 10. The vertical axis represents the area of the tumor region, and the horizontal axis represents the number of days elapsed from SK-MEL-124 cell inoculation.
Figure 14C:
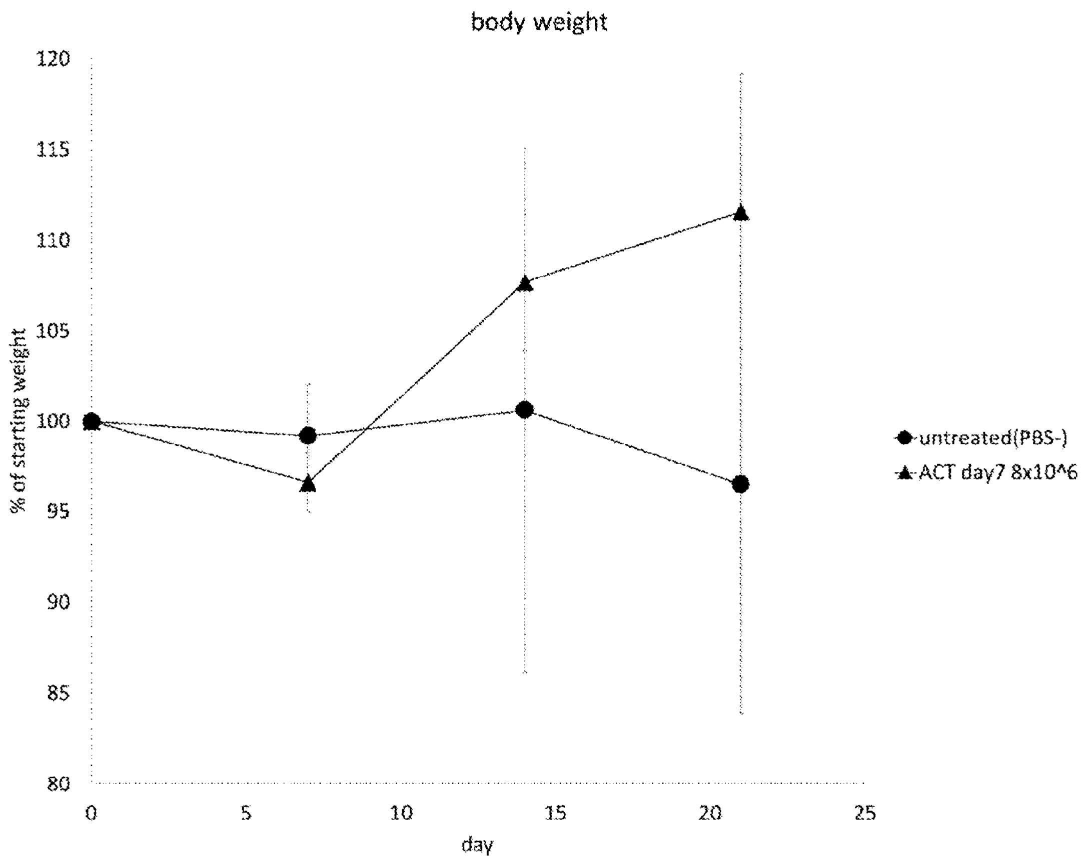
FIG. 14*c* shows the measurement results of the body weight in Test Example 10. The vertical axis represents the relative value of body weight, and the horizontal axis represents the number of days elapsed from SK-MEL-124 cell inoculation.

The results show that in the CAR-T cell infusion group, suppression of the growth of the SK-MEL-124 cells (A24-positive PRAME-positive) was observed in the 3 mice (FIG. 14*b*). In contrast, cancer growth was observed in the untreated group. Thus, the antitumor effect of the infused cells observed in this test is believed to be due to the #98 CAR-T cells. In the mice, there was no obvious body weight loss, and no notable GVHD effect was observed (FIG. 14*c*).

Test Example 11: Cancer Suppression 2 by #98 zG CAR-T Cells

Figure 15A:
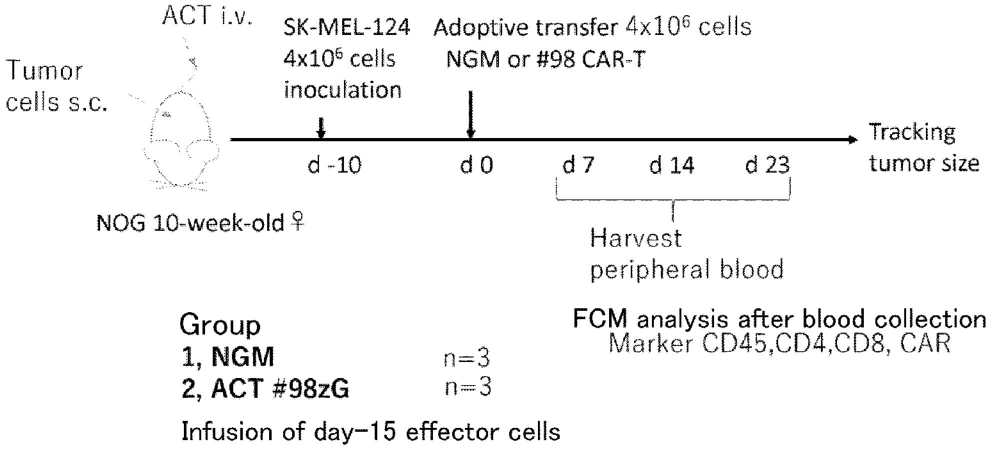
FIG. 15*a* shows the outline of the test of Test Example 11.

Since NOG mice, which were used in the test for cancer suppression by #98 zG CAR-T cells of Test Example 10, lack a common γ receptor, there are no NK cells in the mice. Thus, NOG mice show notably better engraftment of human cells and human tissues than NOD-SCID mice, and human cancer and human normal tissues can be engrafted in NOG mice at high rates. In addition, human T-cell differentiation is observed after transplantation of human hematopoietic stem cells; thus, demand for NOG mice as human immune system model mice is increasing. The characteristics of NOG mice include deletion of T cells and B cells, deletion of natural killer (NK) cells, reduced dendritic cell function, reduced macrophage function, loss of complement activity, and no leakiness of T cells and B cells associated with aging. SK-MEL-1 24 (A24-positive PRAME-positive) cells were transplanted into the right flank of NOG mice at $4\times10^6$ cells/mouse. On day 10 after transplantation, NGM and PRAME #98 CAR-T cells were infused into the mice via a tail vein at $4\times10^6$ cells/mouse. The details are as follows (the outline is shown in FIG. 15*a*). 7-week-old female NOG mice were purchased and acclimated for 3 weeks, and $4\times10^6$ SK-MEL-124 cells were transplanted into the mice by subcutaneous injection. Effector cells were infused into the mice by intravenous administration on day 10 after target cell inoculation. NGM was infused into the control.

Gene transfer to CAR-T cells was performed according to the method of Test Example 8. CD8 and CD4 were present at 91.0% and 6.5%, and the CAR positive percentage was 78.5% for CD8 and 56.9% for CD4.

An experiment was performed in the CAR-T cell infusion group (n=3) and NGM group (n=3), and the tumor diameter was measured every 3 to 4 days. Measurement was performed until day 46 after tumor transplantation.

Figure 15B:
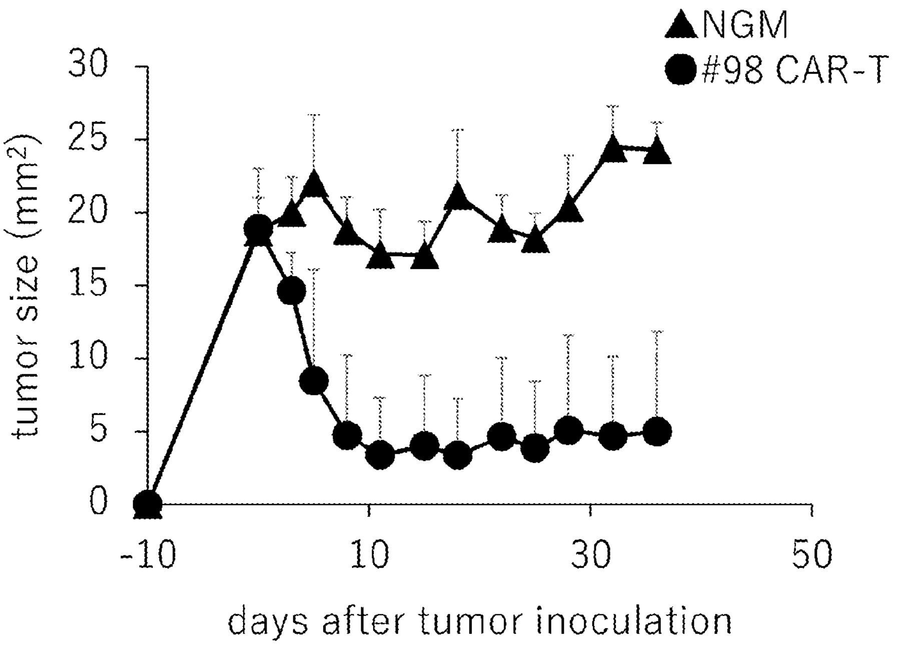
FIG. 15*b* shows the measurement results of the tumor size in Test Example 11. The vertical axis represents the tumor size, and the horizontal axis represents the number of days elapsed from SK-MEL-124 cell inoculation (~10).
Figure 15C:
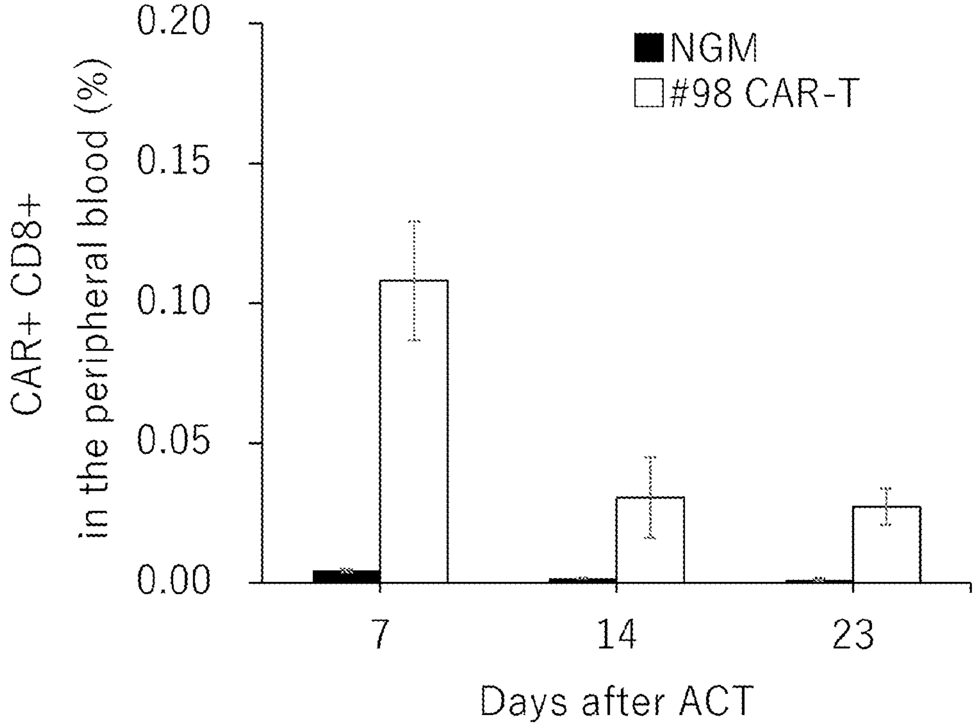
FIG. 15*c* shows the measurement results of the proportion of CAR-T cells in Test Example 11. The vertical axis represents the proportion of CAR-T cells in peripheral blood, and the horizontal axis represents the number of days elapsed from SK-MEL-124 cell inoculation.

The results show that in the CAR-T cell infusion group, suppression of the growth of the SK-MEL-124 cells (A24-positive PRAME-positive) was observed in the 3 mice (FIG. 15*b*). In contrast, cancer growth was observed in the NGM group. Thus, the antitumor effect of the infused cells observed in this test is believed to be due to the #98 CAR T cells. After infusion of the NGM and the CAR-T cells, on day 7, day 14, and day 23, orbital blood was collected, and PBMCs were isolated, stained for hCD45 and CD8 CD4 CAR, and analyzed by FACS. The presence of the CAR-T cells was also observed in peripheral blood on day 23 (FIG. 15*c*).

The invention claimed is:

1. A PRAME-binding molecule comprising a heavy-chain variable region containing a heavy-chain CDR1 comprising the amino acid sequence represented by SEQ ID NO: 1, a heavy-chain CDR2 comprising the amino acid sequence represented by SEQ ID NO: 2, and a heavy-chain CDR3 comprising the amino acid sequence represented by SEQ ID NO: 3, and a light-chain variable region containing a light-chain CDR1 comprising the amino acid sequence represented by SEQ ID NO: 9, a light-chain CDR2 comprising the amino acid sequence represented by SEQ ID NO: 10, and a light-chain CDR3 comprising the amino acid sequence represented by SEQ ID NO: 11.

2. The PRAME-binding molecule according to claim 1, which has binding capability to an HLA-A24 PRAMEp301-309 pMHC complex.

3. The PRAME-binding molecule according to claim 1, wherein the binding capability of the PRAME-binding molecule to a peptide consisting of the amino acid sequence represented by SEQ ID NO: 19, a peptide consisting of the amino acid sequence represented by SEQ ID NO: 20, a peptide consisting of the amino acid sequence represented by SEQ ID NO: 21, a peptide consisting of the amino acid sequence represented by SEQ ID NO: 23, a peptide consisting of the amino acid sequence represented by SEQ ID NO: 24, a peptide consisting of the amino acid sequence represented by SEQ ID NO: 25, and a peptide consisting of the amino acid sequence represented by SEQ ID NO: 26 is equal to or less than ½ of the binding capability of the PRAME-binding molecule to a peptide consisting of the amino acid sequence represented by SEQ ID NO: 17.

4. The PRAME-binding molecule according to claim 1, which is a chimeric antigen receptor.

5. The PRAME-binding molecule according to claim 4, comprising a core domain containing an scFv domain that contains the heavy-chain variable region and the light-chain variable region, a transmembrane domain, and an intracellular domain of TCR.

6. The PRAME-binding molecule according to claim 5, wherein the core domain further contains an intracellular domain of a co-stimulator.

7. The PRAME-binding molecule according to claim 1, which is an antibody.

8. A polynucleotide encoding the PRAME-binding molecule according to claim 1.

9. A cell comprising the polynucleotide according to claim 8.

10. A lymphocyte cell comprising a polynucleotide encoding the PRAME-binding molecule according to claim 1.

11. A pharmaceutical composition comprising the lymphocyte cell according to claim 10.

12. A method of treating cancer in a subject in need thereof, the method comprising administering the pharmaceutical composition according to claim 11 to the subject in need thereof.

* * * * *